(12) United States Patent
Liphardt et al.

(10) Patent No.: US 7,304,737 B1
(45) Date of Patent: *Dec. 4, 2007

(54) ROTATING OR ROTATABLE COMPENSATOR SYSTEM PROVIDING ABERATION CORRECTED ELECTROMAGNETIC RAADIATION TO A SPOT ON A SAMPLE AT MULTIPLE ANGLES OF A INCIDENCE

(75) Inventors: Martin M. Liphardt, Lincoln, NE (US); Blaine D. Johs, Lincoln, NE (US); Jeffrey S. Hale, Lincoln, NE (US); Craig M. Herzinger, Lincoln, NE (US); Steven E. Green, Lincoln, NE (US); Ping He, Lincoln, NE (US); John A. Woollam, Lincoln, NE (US)

(73) Assignee: J.A. Woollam Co., Inc, Lincoln, NE (US)

( * ) Notice: Subject to any disclaimer, the term of this patent is extended or adjusted under 35 U.S.C. 154(b) by 1 day.

This patent is subject to a terminal disclaimer.

(21) Appl. No.: 11/497,920

(22) Filed: Aug. 3, 2006

Related U.S. Application Data

(63) Continuation-in-part of application No. 11/397,393, filed on Apr. 5, 2006, and a continuation-in-part of application No. 10/928,904, filed on Aug. 27, 2004, now abandoned, and a continuation-in-part of application No. 10/699,540, filed on Nov. 1, 2003, now Pat. No. 7,158,231, and a continuation-in-part of application No. 10/034,800, filed on Dec. 28, 2001, now Pat. No. 6,822,738, and a continuation-in-part of application No. 09/945,962, filed on Sep. 4, 2001, now Pat. No. 7,075,649, and a continuation-in-part of application No. 09/583,229, filed on May 30, 2000, now Pat. No. 6,804,004, and a continuation-in-part of application No. 09/517,125, filed on Feb. 29, 2000, now abandoned, and a continuation-in-part of application No. 09/419,794, filed on Oct. 18, 1999, now Pat. No. 6,549,282, and a continuation-in-part of application No. 09/246,888, filed on Feb. 8, 1999, now Pat. No. 6,084,675, and a continuation-in-part of application No. 09/162,217, filed on Sep. 29, 1998, now Pat. No. 6,034,777, and a continuation-in-part of application No. 09/144,764, filed on Aug. 31, 1998, now Pat. No. 5,969,818, and a continuation-in-part of application No. 09/033,694, filed on Mar. 3, 1998, now Pat. No. 5,963,327, and a continuation-in-part of application No. 08/912,211, filed on Aug. 15, 1997, now Pat. No. 5,872,630, and a continuation-in-part of application No. 08/618,820, filed on Mar. 20, 1996, now Pat. No. 5,706,212, which is a continuation-in-part of application No. 08/530,892, filed on Sep. 20, 1995, now Pat. No. 5,666,201, application No. 11/497,920, and a continuation-in-part of application No. 09/232,257, filed on Jan. 19, 1999, now Pat. No. 6,141,102, and a continuation-in-part of application No. 09/225,118, filed on Jan. 4, 1999, now Pat. No. 6,084,674, and a continuation-in-part of application No. 09/223,822, filed on Jan. 4, 1999, now Pat. No. 6,118,537, and a continuation-in-part of application No. 09/225,371, filed on Jan. 4, 1999, now Pat. No. 6,100,981, and a continuation-in-part of application No. 09/225,076, filed on Jan. 4, 1999, now Pat. No. 5,963,325.

(60) Provisional application No. 60/527,638, filed on Dec. 8, 2003, provisional application No. 60/527,554, filed on Dec. 6, 2003, provisional application No. 60/497,492, filed on Aug. 25, 2003, provisional application No. 60/094,104, filed on Jul. 24, 1998.

(51) Int. Cl.
*G01J 4/00* (2006.01)

(52) U.S. Cl. .................................................. 356/369

(58) Field of Classification Search ................... None
See application file for complete search history.

(56) References Cited

U.S. PATENT DOCUMENTS

| 548,495 A | 10/1895 | Abbe |
| 2,447,828 A | 8/1948 | West ........................ 359/495 |

| | | | |
|---|---|---|---|
| 3,748,015 A | 7/1973 | Offner | 359/366 |
| 3,817,624 A | 6/1974 | Martin | 356/138 |
| 4,053,232 A | 10/1977 | Dill et al. | 356/11 F |
| 4,054,812 A | 10/1977 | Lessner et al. | 313/44 |
| 4,176,951 A | 12/1979 | Robert et al. | 356/33 |
| 4,179,217 A | 12/1979 | Robert et al. | 356/33 |
| 4,322,165 A | 3/1982 | Ellebracht et al. | 356/316 |
| 4,556,292 A | 12/1985 | Mathyssek et al. | 350/394 |
| 4,650,315 A | 3/1987 | Markle | 355/43 |
| 4,668,086 A | 5/1987 | Redner | 356/33 |
| 4,688,904 A | 8/1987 | Hirose et al. | 359/729 |
| 4,770,895 A | 9/1988 | Hartley | 427/10 |
| 4,772,104 A | 9/1988 | Buhrer | 350/403 |
| 4,875,773 A | 10/1989 | Burns et al. | 356/328 |
| 4,917,461 A | 4/1990 | Goldstein | 350/286 |
| 4,961,634 A | 10/1990 | Chipman | 350/403 |
| 5,016,980 A | 5/1991 | Waldron | 350/286 |
| 5,045,704 A | 9/1991 | Coates | 250/372 |
| 5,091,320 A | 2/1992 | Aspnes et al. | 427/8 |
| 5,136,413 A | 8/1992 | MacDonald et al. | 359/213 |
| 5,166,752 A | 11/1992 | Spanier et al. | 356/319 |
| 5,229,833 A | 7/1993 | Stewart | 356/352 |
| 5,329,357 A | 7/1994 | Bernoux et al. | 356/369 |
| RE34,783 E | 11/1994 | Coates | 250/372 |
| 5,373,359 A | 12/1994 | Woollam et al. | 356/328 |
| 5,475,525 A | 12/1995 | Tournois et al. | 359/245 |
| 5,486,701 A | 1/1996 | Norton et al. | 250/372 |
| 5,504,582 A | 4/1996 | Johs et al. | 356/369 |
| 5,521,706 A | 5/1996 | Green et al. | 356/369 |
| 5,581,350 A | 12/1996 | Chen et al. | 356/369 |
| 5,596,406 A | 1/1997 | Rosencwaig et al. | 356/327 |
| 5,608,526 A | 3/1997 | Piwonka-Corle et al. | 356/369 |
| 5,666,201 A | 9/1997 | Johs | 356/369 |
| 5,706,212 A | 1/1998 | Thompson et al. | 364/525 |
| 5,793,480 A | 8/1998 | Lacey et al. | 356/73 |
| 5,818,596 A | 10/1998 | Imai et al. | 356/630 |
| 5,859,424 A | 1/1999 | Norton | 250/226 |
| 5,872,630 A | 2/1999 | Johs et al. | 356/369 |
| 5,877,859 A | 3/1999 | Aspnes et al. | 356/364 |
| 5,910,842 A | 6/1999 | Piwonka-Corle et al. | 356/369 |
| 5,917,594 A | 6/1999 | Norton | 356/327 |
| 5,929,995 A | 7/1999 | Johs | 356/369 |
| 5,946,098 A | 8/1999 | Johs et al. | 356/364 |
| 5,963,325 A | 10/1999 | Johs et al. | 356/364 |
| 5,973,787 A | 10/1999 | Aspnes et al. | 356/369 |
| 6,031,619 A | 2/2000 | Wilkens et al. | 356/419 |
| 6,034,777 A | 3/2000 | Johs et al. | 356/369 |
| 6,084,674 A | 7/2000 | Johs et al. | 356/364 |
| 6,084,675 A | 7/2000 | Herzinger et al. | 356/369 |
| 6,100,981 A | 8/2000 | Johs et al. | 356/364 |
| 6,118,537 A | 9/2000 | Johs et al. | 356/369 |
| 6,134,012 A | 10/2000 | Aspnes et al. | 356/369 |
| 6,141,100 A | 10/2000 | Burka et al. | 356/451 |
| 6,141,102 A | 10/2000 | Johs et al. | 356/364 |
| 6,181,421 B1 | 1/2001 | Aspnes et al. | 356/369 |
| 6,256,097 B1 * | 7/2001 | Wagner | 356/369 |
| 6,278,519 B1 * | 8/2001 | Rosencwaig et al. | 356/369 |
| 6,320,657 B1 | 11/2001 | Aspnes et al. | 356/369 |
| 6,353,477 B1 | 3/2002 | Johs et al. | 356/369 |
| 6,414,302 B1 | 7/2002 | Freeouf | 250/225 |
| 6,493,097 B1 | 12/2002 | Ivarsson | 356/630 |
| 6,734,967 B1 | 5/2004 | Piwonka-Corle et al. | 356/369 |
| 6,744,505 B1 | 6/2004 | Wang et al. | 356/326 |
| 6,835,933 B2 | 12/2004 | Lin et al. | 250/339.05 |
| 7,190,460 B2 * | 3/2007 | Wang | 356/446 |
| 2002/0149774 A1 | 10/2002 | McAnich | |
| 2003/0071996 A1 | 4/2003 | Wang et al. | |
| 2003/0150997 A1 | 8/2003 | Eckert et al. | |
| 2004/0125369 A1 | 7/2004 | Wang | |

FOREIGN PATENT DOCUMENTS

| WO | WO 01/086257 | 11/2001 |
|---|---|---|
| WO | WO 01/90687 A2 | 11/2001 |

OTHER PUBLICATIONS

J.A. Woollam Co. Flyer on VUV-Vase.

* cited by examiner

*Primary Examiner*—Tu T. Nguyen
(74) *Attorney, Agent, or Firm*—James D. Welch

(57) ABSTRACT

Spectroscopic ellipsometer systems which include polarizer and analyzer elements which remain fixed in position during data acquisition while at least one continuously rotating or step-wise rotatable compensator imposes a continuously variable or plurality of sequentially discrete polarization states on a beam of electromagnetic radiation, including a system of mirrors and refractive elements for correcting aberation while directing a beam of electromagnetic radiation to a spot on a sample at a multiple different angles-of-incidence.

17 Claims, 12 Drawing Sheets

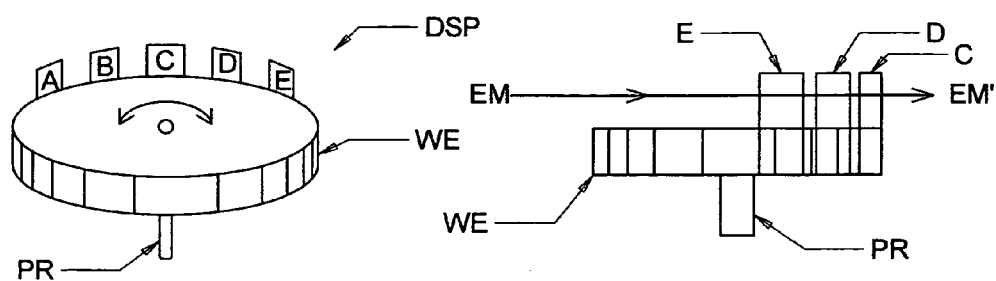
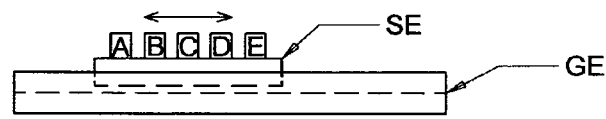
FIG. 3a
FIG. 3b
FIG. 3c
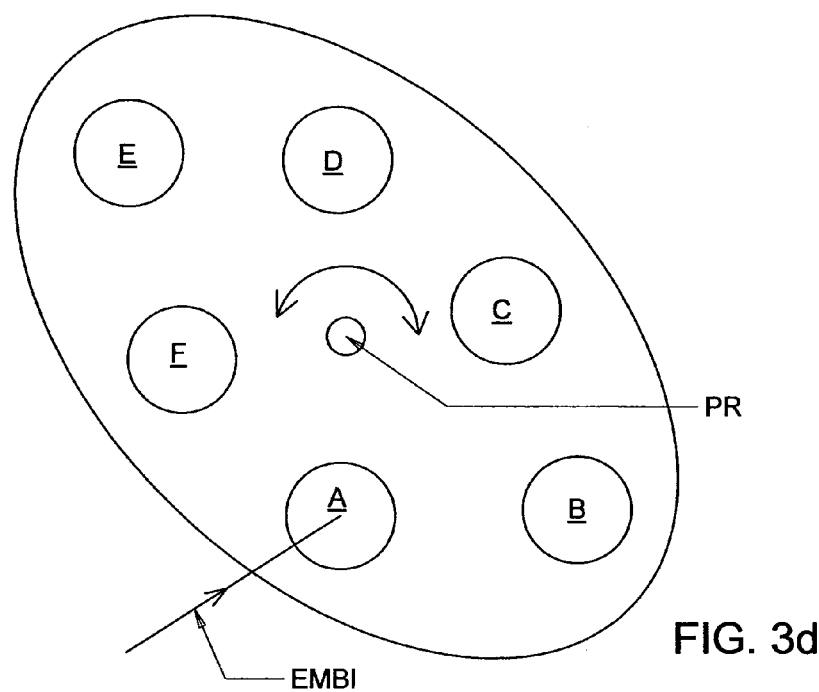
FIG. 3d

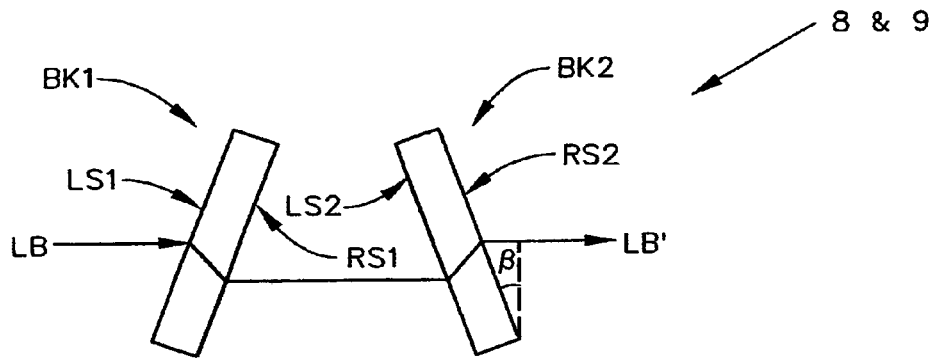
FIG. 3n₁
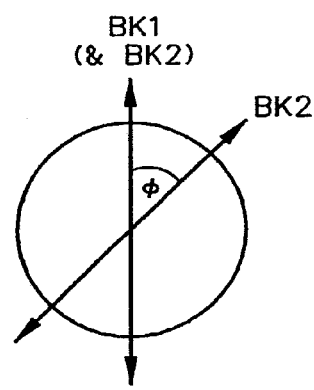
FIG. 3n₂
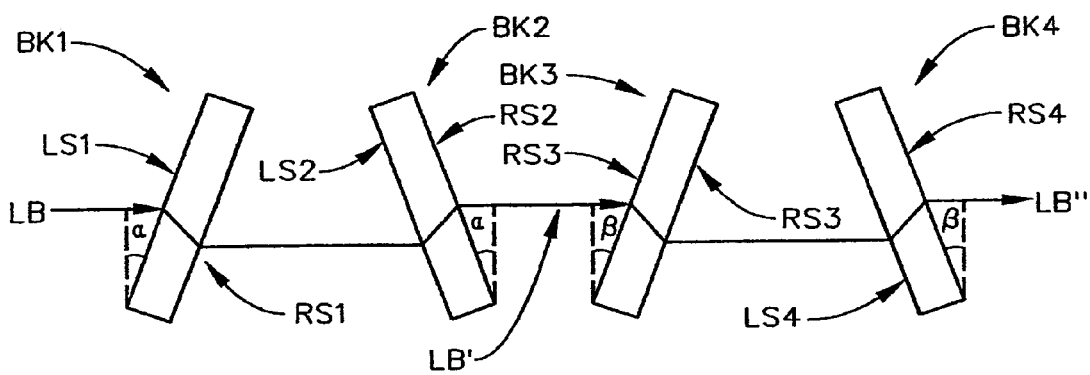
FIG. 3o₁

FIG. 3o$_2$

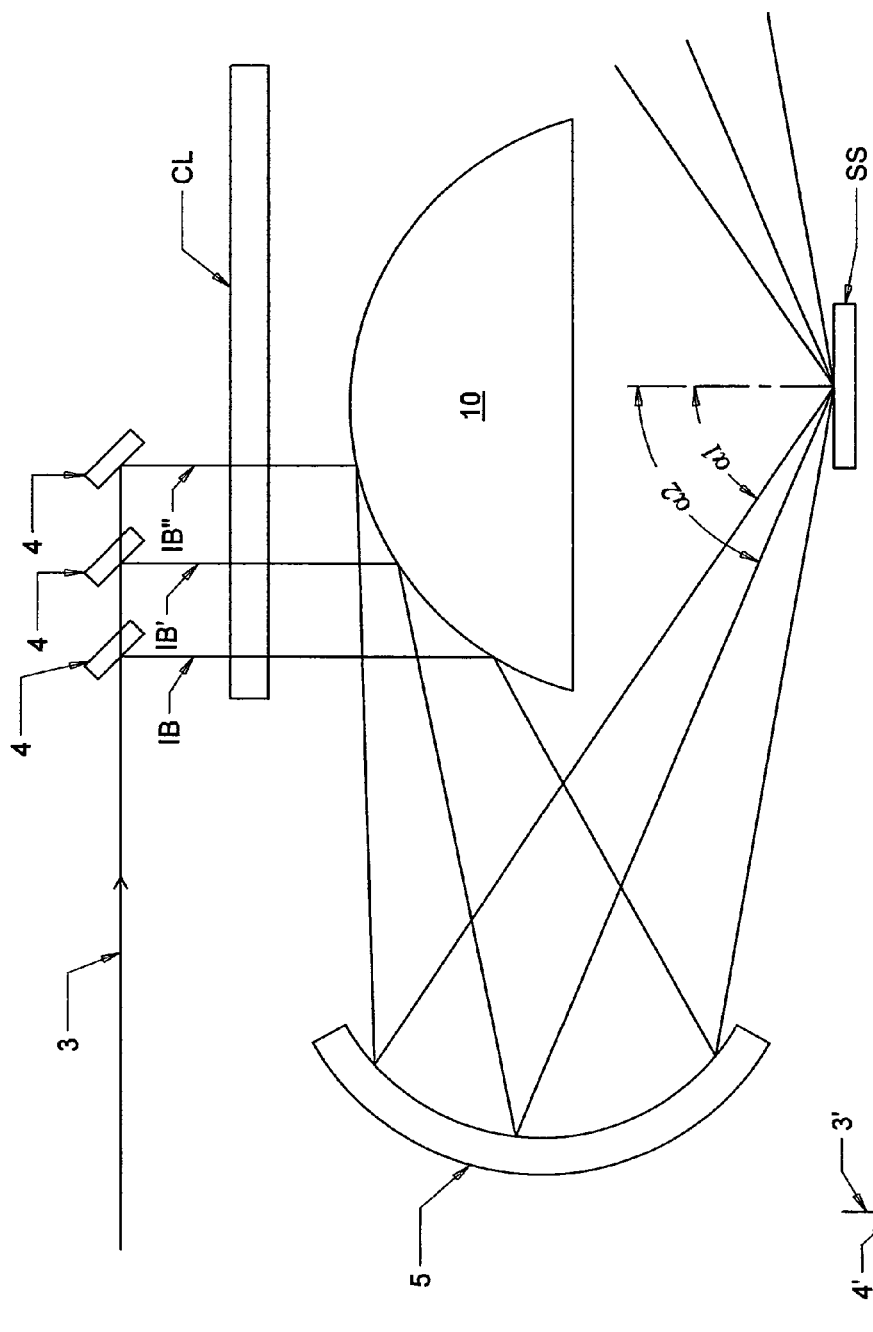
FIG. 11
FIG. 12
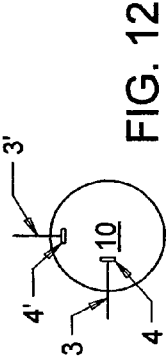

ROTATING OR ROTATABLE COMPENSATOR SYSTEM PROVIDING ABERATION CORRECTED ELECTROMAGNETIC RAADIATION TO A SPOT ON A SAMPLE AT MULTIPLE ANGLES OF A INCIDENCE

This application is a CIP of Ser. No. 11/397,393 Filed Apr. 5, 2006; and therevia of Ser. No. 10/928,904 Filed Aug. 27, 2004 now abandoned, and therevia Claims Benefit of Provisional Application Ser. No. 60/497,492 Filed Aug. 25, 2003.

This application is also a CIP of Ser. No. 10/928,904 Filed Aug. 27, 2004, and therevia Claims Benefit of Provisional Application Ser. No. 60/497,492 Filed Aug. 25, 2003.

This application is further a Continuation-in-Part of application Ser. No. 10/034,800 Filed Dec. 28, 2001 now U.S. Pat. No. 6,822,738 and of application Ser. No. 09/583,229 Filed May 30, 2000 now U.S. Pat. No. 6,804,004 and therevia of Ser. No. 09/162,217 Filed Sep. 29, 1998 (now U.S. Pat. No. 6,034,777), of Ser. No. 09/033,694 Filed Mar. 3, 1998 (now U.S. Pat. No. 5,963,327); of Ser. No. 09/144,764 Filed Aug. 31, 1998 (now U.S. Pat. No. 5,969,818), of Ser. No. 09/419,794 Filed Oct. 18, 1999 now U.S. Pat. No. 6,549,282, and therevia Claims benefit of Provisional 60/094,104 Filed Jul. 24, 1998.

This application further is a Continuation-in-Part of application Ser. No. 10/699,540 Filed Nov. 1, 2003 now U.S. Pat. No. 7,158,231 and therevia of application Ser. No. 09/945,962 Filed Sep. 4, 2001 now U.S. Pat. No. 7,075,649, application Ser. No. 09/517,125 Filed Feb. 29, 2000 now abandoned, and therevia of application Ser. No. 09/246,888 filed Feb. 8, 1999, (now U.S. Pat. No. 6,084,675). Further, via the Ser. No. 09/246,888 application, this application is a Continuation-In-Part of application Ser. No. 08/912,211 filed Aug. 15, 1997, (now U.S. Pat. No. 5,872,630), which was a CIP from application Ser. No. 08/530,892 filed Sep. 20, 1995, (now U.S. Pat. No. 5,666,201); and is a CIP of application Ser. No. 08/618,820 filed Mar. 20, 1996, (now U.S. Pat. No. 5,706,212). This application is further a CIP of application Ser. Nos. 09/225,118, (now U.S. Pat. No. 6,084,674); 09/223,822, (now U.S. Pat. No. 6,118,537); 09/232,257, (now U.S. Pat. No. 6,141,102); 09/225,371, (now U.S. Pat. No. 6,100,981); 09/225,076, (now U.S. Pat. No. 5,963,325), which applications depend from application Ser. No. 08/997,311 filed Dec. 23, 1997, (now U.S. Pat. No. 5,946,098).

This application also Claims benefit of Provisional Application Ser. No. 60/527,554, Filed Dec. 6, 2003; and 60/527,638 Filed Dec. 8, 2003.

TECHNICAL FIELD

The present invention relates to ellipsometer systems, and more particularly to ellipsometer systems comprising transmissive rotating or stepwise rotatable compensators for continuously or step-wise varying polarization states and further comprising transmissive multi-element lens focusing of a spectroscopic electromagnetic beam into a small, chromatically relatively undispersed area spot on a sample system. The ellipsometer system optionally is present in an environmental control chamber.

BACKGROUND

The practice of ellipsometry is well established as a non-destructive approach to determining characteristics of sample systems, and can be practiced in real time. The topic is well described in a number of publications, one such publication being a review paper by Collins, titled "Automatic Rotating Element Ellipsometers: Calibration, Operation and Real-Time Applications", Rev. Sci. Instrum., 61(8) (1990).

In general, modern practice of ellipsometry typically involves causing a spectroscopic beam of electromagnetic radiation, in a known state of polarization, to interact with a sample system at least one angle of incidence with respect to a normal to a surface thereof, in a plane of incidence. (Note, a plane of incidence contains both a normal to a surface of an investigated sample system and the locus of said beam of electromagnetic radiation). Changes in the polarization state of said beam of electromagnetic radiation which occur as a result of said interaction with said sample system are indicative of the structure and composition of said sample system. The practice of ellipsometry further involves proposing a mathematical model of the ellipsometer system and the sample system investigated by use thereof, and experimental data is then obtained by application of the ellipsometer system. This is typically followed by application of a square error reducing mathematical regression to the end that parameters in the mathematical model which characterize the sample system are evaluated, such that the obtained experimental data, and values calculated by use of the mathematical model, are essentially the same.

A typical goal in ellipsometry is to obtain, for each wavelength in, and angle of incidence of said beam of electromagnetic radiation caused to interact with a sample system, sample system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$), caused by interaction with said sample system. The basic equation relating PSI and DELTA is:

$$\rho = rp/rs - \mathrm{Tan}(\Psi)\exp(i\Delta)$$

As alluded to, the practice of ellipsometry requires that a mathematical model be derived and provided for a sample system and for the ellipsometer system being applied. In that light it must be appreciated that an ellipsometer system which is applied to investigate a sample system is, generally, sequentially comprised of:

a. a Source of a beam electromagnetic radiation;
b. a Polarizer element;
c. optionally a compensator element;
d. (additional element(s));
e. a sample system;
f. (additional element(s));
g. optionally a compensator element;
h. an Analyzer element; and
i. a Spectroscopic Detector System.

Each of said components b.-i. must be accurately represented by a mathematical model of the ellipsometer system along with a vector which represents a beam of electromagnetic radiation provided from said source of a beam electromagnetic radiation, Identified in a. above)

Various conventional ellipsometer configurations provide that a Polarizer, Analyzer and/or Compensator(s) can be rotated during data acquisition, and are describe variously as Rotating Polarizer (RPE), Rotating Analyzer (RAE) and Rotating Compensator (RCE) Ellipsometer Systems. As described elsewhere in this Specification, the present invention provides that no element must be continuously rotated during data acquisition but rather that a sequence of discrete polarization states can be imposed during data acquisition. This approach allows eliminating many costly components from conventional rotating element ellipsometer systems, and, hence, production of an "Ultra-Low-Complexity" ellipsometer system. It is noted, that nulling ellipsometers also exist in which elements therein are rotatable in use, rather than rotating. Generally, use of a nulling ellipsometer system involves imposing a linear polarization state on a beam of electromagnetic radiation with a polarizer, causing the resulting polarized beam of electromagnetic radiation to interact with a sample system, and then adjusting an analyzer to an azimuthal azimuthal angle which effectively cancels out the beam of electromagnetic radiation which proceeds past the sample system. The azimuthal angle of the analyzer at which nulling occurs provides insight to properties of the sample system.

It is further noted that reflectometer systems are generally sequentially comprised of:
   a. a Source of a beam electromagnetic radiation;
   d. (optional additional element(s));
   e. a sample system;
   f. (optional additional element(s));
   i. a Spectroscopic Detector System;

and that reflectometer systems monitor changes in intensity of a beam of electromagnetic radiation caused to interact with a sample system. That is, the ratio of, and phase angle between, orthogonal components in a polarized beam are not of direct concern.

Continuing, in use, data sets can be obtained with an ellipsometer system configured with a sample system present, sequentially for cases where other sample systems are present, and where an ellipsometer system is configured in a straight-through configuration wherein a beam of electromagnetic radiation is caused to pass straight through the ellipsometer system without interacting with a sample system. Simultaneous mathematical regression utilizing multiple data sets can allow evaluation of sample system characterizing PSI and DELTA values over a range of wavelengths. The obtaining of numerous data sets with an ellipsometer system configured with, for instance, a sequence of sample systems present and/or wherein a sequential plurality of polarization states are imposed on an electromagnetic beam caused to interact therewith, can allow system calibration of numerous ellipsometer system variables.

Patents of which the Inventor is aware include those to Woollam et al, U.S. Pat. No. 5,373,359, patent to Johs et al. U.S. Pat. No. 5,666,201 and patent to Green et al., U.S. Pat. No. 5,521,706, and patent to Johs et al., U.S. Pat. No. 5,504,582 are disclosed for general information as they pertain to ellipsometer systems.

Further patents of which the Inventor is aware include U.S. Pat. Nos. 5,757,494 and 5,956,145 to Green et al., in which are taught a method for extending the range of Rotating Analyzer/Polarizer ellipsometer systems to allow measurement of DELTA'S near zero (0.0) and one-hundred-eighty (180) degrees, and the extension of modulator element ellipsometers to PSI'S of forty-five (45) degrees. Said patents describes the presence of a variable, transmissive, bi-refringent component which is added, and the application thereof during data acquisition to enable the identified capability.

A patent to Thompson et al. U.S. Pat. No. 5,706,212 is also disclosed as it teaches a mathematical regression based double Fourier series ellipsometer calibration procedure for application, primarily, in calibrating ellipsometers system utilized in infrared wavelength range. Bi-refringent, transmissive window-like compensators are described as present in the system thereof, and discussion of correlation of retardations entered by sequentially adjacent elements which do not rotate with respect to one another during data acquisition is described therein.

A patent to He et al., U.S. Pat. No. 5,963,327 is disclosed as it describes an ellipsometer system which enables providing a polarized beam of electromagnetic radiation at an oblique angle-of-incidence to a sample system in a small spot area.

A patent to Johs et al., U.S. Pat. No. 5,872,630 is disclosed as it describes an ellipsometer system in which an analyzer and polarizer are maintained in a fixed in position during data acquisition, while a compensator is caused to continuously rotate.

Patent to Dill et al., U.S. Pat. No. 4,953,232 is disclosed as it describes a rotating compensator ellipsometer system.

Patents co-owned with this application, which patents Claim various Compensator Designs recited in Claims herein, and which patents are incorporated hereinto by reference are:
   U.S. Pat. No. 5,946,098 to Johs et al.;
   U.S. Pat. No. 5,963,325 to Johs et al.;
   U.S. Pat. No. 6,084,674 to Johs et al.;
   U.S. Pat. No. 6,084,675 to Herzinger et al.;
   U.S. Pat. No. 6,100,981 to Johs et al.;
   U.S. Pat. No. 6,118,537 to Johs et al.;
   U.S. Pat. No. 6,141,102 to Johs et al.

Patents cited in examination of said patents included U.S. Pat. No. 4,556,292 to Mathyssek et al. and U.S. Pat. No. 5,475,525 to Tournois et al.

A patent to Coates et al., U.S. Pat. No. 4,826,321 is disclosed as it describes applying a reflected monochromatic beam of plane polarized electromagnetic radiation at a Brewster angle of incidence to a sample substrate to determine the thickness of a thin film thereupon.

Other patents which describe use of reflected electromagnetic radiation to investigate sample systems are Nos. RE 34,783, U.S. Pat. No. 4,373,817, and U.S. Pat. No. 5,045, 704 to Coates; and U.S. Pat. No. 5,452,091 to Johnson.

A patent to Bjork et al., U.S. Pat. No. 4,647,207 is disclosed as it describes an ellipsometer system which has provision for sequentially positioning a plurality of reflective polarization state modifiers in a beam of electromagnetic radiation. While said 207 patent mentions investigating a sample system in a transmission mode, no mention or suggestion is found for utilizing a plurality of transmitting polarization state modifiers, emphasis added. U.S. Pat. No. 4,210,401; 4,332,476 and 4,355,903 are also identified as being cited in the 207 patent. It is noted that systems as disclosed in these patents, (particularly in the 476 patent), which utilize reflection from an element to modify a polarization state can, that if such an element is an essential duplicate of an investigated sample and is rotated ninety degrees therefrom, then the effect of the polarization state modifying element on the electromagnetic beam effect is extinguished by the sample.

A patent to Mansuripur et al., U.S. Pat. No. 4,838,695 is disclosed as it describes an apparatus for measuring reflectivity.

Patents to Rosencwaig et al., U.S. Pat. Nos. 4,750,822 and 5,595,406 are also identified as they describe systems which impinge electromagnetic beams onto sample systems at oblique angles of incidence. The 406 patent provides for use of multiple wavelengths and multiple angles of incidence. For similar reasons U.S. Pat. No. 5,042,951 to Gold et al. is also disclosed.

A patent to Osterberg, U.S. Pat. No. 2,700,918 describes a microscope with variable means for increasing the visibility of optical images, partially comprised of discrete birefringent plates which can be positioned in the pathway between an eyepiece and an observed object. Other patents identified in a Search which identified said 918 patent are U.S. Pat. No. 3,183,763 to Koester; U.S. Pat. No. 4,105,338 to Kuroha; U.S. Pat. No. 3,992,104 to Watanabe and a Russian Patent, No. SU 1518728. Said other patents are not believed to be particularly relevant, however.

A patent, U.S. Pat. No. 5,329,357 to Bernoux et al. is also identified as it Claims use of fiber optics to carry electromagnetic radiation to and from an ellipsometer system which has at least one polarizer or analyzer which rotates during data acquisition. It is noted that if both the polarizer and analyzer are stationary during data acquisition that this patent is not controlling where electromagnetic radiation carrying fiber optics are present.

Patents identified in a Search specifically focused on the use of lenses, preferrably achromatic, in ellipsometry and related systems are:

U.S. Pat. Nos. 5,877,859 and 5,798,837 to Aspnes et al.;
U.S. Pat. No. 5,333,052 to Finarov;
U.S. Pat. No. 5,608,526 to Piwonka-Corle et al.;
U.S. Pat. No. 5,793,480 to Lacy et al.;
U.S. Pat. Nos. 4,636,075 and 4,893,932 to Knollenberg; and
U.S. Pat. No. 4,668,860 to Anthon.

A patent, U.S. Pat. No. 5,917,594 to Norton describes a system which utilizes a spherical mirror to focus an electromagentic beam onto the surface of a sample in the form of a small spot. A relevant aspect of the 594 patent system is that a positive lens and a negative meniscus lens are combined and placed into the pathway of the electromagnetic beam prior to its reflection from a focusing spherical mirror. The purpose of doing so is to make the optical system, as a whole, essentially achromatic in the visible wavelength range, and even into the ultraviolet wavelength range. It is further stated that the power of the combined positive lens and negative meniscus lens is preferrably zero.

Additional patents, which provide insight to reflective optics are disclosed below.

Patents to Coates U.S. Pat. No. 5,045,704 and RE: 34,783, for example, describe a system which applies a reflective objective lens to direct electromagnetic radiation provided to it by a convex reflective element to a spot on a sample. Said electromagnetic radiation is provided to said convex reflective element via a beam splitter. It is noted that the concave reflective objective lens disclosed in said Coates patents is of a donut shape, which can be more difficult to manufacture than a plurality of spherical concave mirrors.

Additional patents to Norton et al. include U.S. Pat. Nos. 5,486,701 and 5,859,424, and a patent to Piwonka-Corle et al., U.S. Pat. No. 5,608,526. Said patents describe use of spherical reflective focusing elements to converge a beam of electromagnetic radiation into a small spot on a sample.

U.S. Pat. No. 6,744,505 B1 to Wang et al. is disclosed as it describes use of a concave reflecting optics to direct diverging diffracted electromagnetic radiation into a collimated beam which enters a detector. Further disclosed is a Published Application of Wang et al. is U.S. Pat. No. 2004/0125369 A1.

U.S. Pat. No. 3,748,015 to Offner is disclosed as it describes an imaging system comprising a concave spherical mirror and a convex spherical mirror; said elements being arranged such that electromagnetic radiation caused to approach the concave spherical reflects at a first location thereon is reflected to said a convex spherical mirror, from which it reflects onto a second location of said concave spherical mirror, from which it reflects as a beam of electromagnetic radiation, which, if the electromagnetic radiation caused to approach the concave spherical mirror at a first location was, for instance, an imaged aperture, appears as a small spot on the sample. It is emphasized that a collimated electromagnetic beam is not "focused" by the 1:1 imager, but rather a substantially point source is imaged thereby.

Patents identified by the Examiner in examination of the Parent application Ser. No. 10/928,904 are: U.S. Pat. No. 4,650,315 to Markle; U.S. Pat. No. 6,835,933 to Lin et al.; U.S. Pat. No. 5,136,413 to MacDonald et al.; U.S. Pat. No. 4,688,904 to Hirose et al.; U.S. Pat. No. 6,141,100 to Burka et al. U.S. Pat. No. 6,522,404 to Wilson et al.; U.S. Pat. No. 5,880,834 to Chrisp; U.S. Pat. No. 6,600,560 to Mikkelsen et al.; U.S. Pat. No. 6,522,717 to Murakami et al.; U.S. Pat. No. 5,715,061 to Fujiwara; EPO 0 452 963 A2 BY Diapon Screen Mfg. Co.

An additional clever combination of refractive and reflective optics to provide aberation corrected small spots of electromagnetic radiation onto samples would provide utility, particularly if it allowed selection of angles-of-incidence at which a beam impinges on a sample, and even in view of relevant prior art, there remains need for a spectroscopic ellipsometer system which:

presents with a source of spectroscopic electromagnetic radiation and a spectroscopic multi-element detector system;

comprises polarizer and analyzer which remain stationary during data acquisition;

utilizes a plurality of transmissive step-wise rotatable or rotating compensator means to effect a plurality of sequential polarization states during said data acquisition;

which includes at least one reflective optics for focusing electromagnetic radiation onto a spot on a sample, simultaneously or sequentially at a plurality of angles-of-incidence and;

which comprise at least one transmissive abberation correction means.

In particular, need ramains for a system comprising reflective optics in the context of rotating or rotatable compensator ellipsometer and the like systems as were taught originally in U.S. Pat. No. 5,872,630 to Johs et al., from which this application is a CIP. The present invention provides a system with the identified attributes.

DISCLOSURE OF THE INVENTION

The present invention is, in the first instance, a spectroscopic ellipsometer system basically comprising:
a source of polychromatic electromagnetic radiation;
a polarizer which is fixed in position during data acquisition;
a stage for supporting a sample system;
an analyzer which is fixed in position during data acquisition; and
a multi-element spectroscopic detector system.

In addition, the present invention ellipsometer system further comprises at least one means for continuously or discretely, sequentially, modifying a polarization state of a beam of electromagnetic radiation through a plurality of polarization states. The at least one means for continuously or discretely, sequentially, modifying a polarization state of a beam of electromagnetic radiation through a plurality of polarization states, is positioned between said polarizer and said stage for supporting a sample system, and/or and between said stage for supporting a sample system and said analyzer, and so that said beam of electromagnetic radiation transmits through a polarization state modifier element thereof in use. The present invention at least one means for continuously or discretely, sequentially, modifying a polarization state of a beam of electromagnetic radiation through a plurality of polarization states comprises a compensator which is mounted to allow rotation about the locus of a beam of electromagentic radiation caused to pass therethrough.

Further, the disclosed invention system sequentially comprises a Beam Directing system comprised of a substantially Planar Mirror, Aberation Correction System means, a Convex Spherical Mirror, at least one Concave Spherical Mirror, and an Aberation Correction System means. In use said substantially Planar Mirror directs a beam of electromagnetic radiation to reflect therefrom and proceed as Beam which reflects from Convex Spherical Mirror to said at least one Concave Spherical Mirror which focuses it, as Incident Beam to a spot on Sample. Reflected electromagnetic radiation from said Spot on said Sample is then collected by the second at least one Concave Spherical Mirrors, which reflectively directs it to reflect from Convex Spherical Mirror so that it emerges as an Output Beam. Said input and output Aberation Correction System means is positioned so that both Input and Output Beams pass therethrough. The Aberation Correction System means is preferably achromatic and of approximately zero power and is necessary because the electromagnetic beams approach and reflect from the spherical mirrors along an off-axis locus. An improvement an be that said substantially Planar Mirror is movable, such as by being mounted to a slider element, so as to enable its directing said beam of electromagnetic radiation toward said Convex Spherical Mirror at different locations thereon, such that it is then caused to approach said sample at determinable angles-of-incidence.

It is further disclosed that duplicate systems, as described above, can be provided and oriented so as to direct a beam of electromagnetic radiation produced thereby toward the Convex Spherical Mirror thereof at an angle offset from the beam of electromagnetic radiation produced by other of said duplicate systems, said offset angle being viewed as a rotation angle from above said Convex Spherical Mirror. Where the substantially Planar Mirror in each system is positioned at a different distance from, for instance the center of the Convex Spherical Mirror, then the beams provided to the Sample by each system are at different angles-of-incidence.

In combination with the just described beam directing system, the present invention further comprises a combination spectroscopic reflectometer/ellipsometer system basically comprising:

a source of polychromatic electromagnetic radiation;
a stage for supporting a sample system;
a multi-element spectroscopic detector system.

The combination spectroscopic reflectometer/ellipsometer system further comprises, in the ellipsometer system portion thereof, a polarizer, (which is fixed in position during data acquisition), present between the source of polychromatic electromagnetic radiation and the stage for supporting a sample system, and an analyzer, (which is fixed in position during data acquisition), present between the stage for supporting a sample system and the multi-element spectroscopic detector system. The ellipsometer system also comprises at least one means for discretely, sequentially, modifying a polarization state of a beam of electromagnetic radiation through a plurality of polarization states present between said polarizer and said stage for supporting a sample system, and/or between said stage for supporting a sample system and said analyzer, and positioned so that said beam of electromagnetic radiation transmits through a polarization state modifier element therein during use.

Additionally, the combination spectroscopic reflectometer/ellipsometer system is configured such that a polychromatic beam of electromagnetic radiation provided by said source of polychromatic electromagnetic radiation can, optionally, be directed to interact with a sample system present on said stage for supporting a sample system without any polarization state being imposed thereupon, and such that a polychromatic beam of electromagnetic radiation also provided by said source of polychromatic electromagnetic radiation can be, optionally simultaneously, directed to interact with a sample system present on said stage for supporting a sample system after a polarization state has been imposed thereupon. The polychromatic beam of electromagnetic radiation without any polarization state imposed thereupon, when directed to interact with a sample system present on said stage for supporting a sample system, is typically caused to approach said sample system at an oblique angle-of-incidence which is between a sample system Brewster angle and a normal to the surface of the sample system. Further, the polychromatic beam of electromagnetic radiation provided by said source of polychromatic electromagnetic radiation upon which a polarization state has been imposed, is typically directed to interact with a sample system present on said stage for supporting a sample system at an angle near the Brewster angle of the sample system being investigated. Either, or both, the polychromatic beam (s) of electromagnetic radiation provided by said source of polychromatic electromagnetic radiation, upon which is imposed a polarization state or upon which no polarization state is imposed, is preferably directed to interact with a sample system present on said stage for supporting a sample system via a fiber optic means.

In view of the foregoing, it is disclosed that a present invention system for monitoring change in:

the intensity of; and/or
the ratio of and/or the phase between orthogonal components in;

a spectroscopic beam of electromagnetic radiation, which is caused by interaction with a sample system (SS) comprises:

a source of electromagnetic radiation (LS);
a beam directing system (BDS) comprising:
a substantially planar mirror (4);
a convex spherical mirror (10);
at least one concave spherical mirror (5) (5'); and
aberation correction system (CL) means;

such that in use substantially planar mirror (4) directs a beam of electromagnetic radiation (3) to reflect therefrom and proceed as a beam (IB) to reflect from convex spherical mirror (10), to said at least one concave spherical mirror (5) which focuses it, as incident beam (6) to a spot (M) on sample (SS), reflected electromagnetic radiation (7) from said spot (M) on said sample (SS) being collected by said at least one concave spherical mirror (5'), which reflectively directs it to reflect from convex spherical mirror (10) and emerge as output beam (OB);

said input (IB) and output (OB) aberation correction system (CL) means being positioned so that both input (IB) and output (OB) beams pass therethrough; and a detector (DET) of electromagnetic radiation;

said system further comprising at least one rotating or rotatable compensator (CMP) (CMP') positioned so that said beam of electromagnetic radiation transmits therethrough;

such that in use, said source (LS) of electromagnetic radiation provides a beam (EBI) of electromagnetic radiation to said beam directing system (BDS), which in turn causes said beam of electromagnetic radiation to interact with said spot (M) on said sample (SS) and then proceed into said detector (DET) of electromagnetic radiation, as said at least one rotating or rotable compensator (CMP) (CMP') is caused to continuously rotate or step through sequence of descrete positions.

During data collection by said detector, said at least one compensator is caused to perform motion selected from the group consisting of:

continuously rotates; and sequentially rotates through a plurality of discrete angles;

around an axis defined by the locus of the spectroscopic electromagnetic beam as it transmits therethrough.

Said system can further comprise a polarizer (P) between said source (LS) of electromagnetic radiation and said beam directing system (BDS), and an analyzer (A) between said beam directing system (BDS) and said detector (DET) of electromagnetic radiation and said system is an ellipsometer, polarimeter or the like system.

Further, the substantially planar mirror (4) can be movable so as to enable its directing said beam of electromagnetic radiation (3) toward said convex spherical mirror (10) at different locations thereon, such that said beam of electromagnetic radiation (3) approaches said sample (SS) at determinable angles-of-incidence.

The aberation correction system (CL) means is preferably achromatic and of approximately zero power, and can comprise a combination of two miniscus lenses and/or a bi-convex lens.

In addition, it is noted that there can be at least one additional beam directing system oriented so as to direct a beam of electromagnetic radiation (3) produced thereby toward the convex spherical mirror (10) thereof at an angle offset from the beam of electromagnetic radiation (3) produced other said duplicate systems, said offset angle being viewed as a rotation angle from above said convex spherical mirror (10).

A preferred at least one compensator (CMP) is characterized by a selection from the group consisting of:

said at least one compensator produces a retardance of between seventy-five (75) and one-hundred-thirty (130) degrees over a range of wavelengths defined by a selection from the group consisting of:

a. between one-hundred-ninety (190) and seven-hundred-fifty (750) nanometers;

b. between two-hundred-forty-five (245) and nine-hundred (900) nanometers;

c. between three-hundred-eighty (380) and seventeen-hundred (1700) nanometers;

d. within a range of wavelengths defined by a maximum wavelength (MAXW) and a minimum wavelength (MINW) wherein the ratio of (MAXW)/(MINW) is at least one-and-eight-tenths (1.8); and said at least one compensator produces a retardation between thirty (30.0) and less than one-hundred-thirty-five (135) degrees over a range of wavelengths specified from MINW to MAXW by a selection from the group consisting of:

a. MINW less than/equal to one-hundred-ninety (190) and MAXW greater than/equal to seventeen-hundred (1700);

b. MINW less than/equal to two-hundred-twenty (220) and MAXW greater than/equal to one-thousand (1000) nanometers;

c. within a range of wavelengths defined by a maximum wavelength (MAXW) and a minimum wavelength (MINW) range where (MAXW)/(MINW) is at least four-and one-half (4.5);

A method of monitoring the effect a sample has on a beam of electromagnetic radiation by interaction therewith, comprising the steps of:

a) providing a system as described above;

b) causing said source of electromagnetic radiation to produce a beam thereof and direct it toward said beam directing system;

c) causing said detector of electromagentic radiation to monitor said beam of electromagnetic radiation after it emerges from said beam directing system and comparing the intensity thereof; and/or the ratio of and/or the phase between orthogonal components therein, to the same attributes of the beam directly provided by the source of said beam of electromagnetic radiation.

An alternative description of a present invention system provides that it is a spectroscopic ellipsometer system comprising:

a source of polychromatic electromagnetic radiation;

a polarizer which remains fixed in position during data acquisition;

a stage for supporting a sample system;

an analyzer which remains fixed in position during data acquisition; and a multi-element spectroscopic detector system;

said spectroscopic ellipsometer system further comprising at least one rotating or rotatable compensator means for sequentially modifying a polarization state of a beam of electromagnetic radiation provided by said source of polychromatic electromagnetic radiation through a plurality of polarization states, said rotating or rotatable compensator for sequentially modifying a polarization state of a beam of electromagnetic radiation provided by said source of polychromatic electromagnetic radiation through a plurality of polarization states being present at least one location selected from the group consisting of:

between said polarizer and said stage for supporting a sample system; and between said stage for supporting a sample system and said analyzer;

and positioned so that said beam of electromagnetic radiation transmits therethrough in use;

said spectroscopic ellipsometer system further comprising, between said polarizer and analyzer, a beam directing system for causeing a beam of electromagentic radiation to impinge on spot on a sample system comprising:

a substantially planar mirror;
a convex spherical mirror;
at least one concave spherical mirror; and
aberation correction system means;
such that in use said substantially planar mirror directs a beam of electromagnetic radiation to reflect therefrom and proceed as a beam to reflect from said convex spherical mirror, to said at least one concave spherical mirror which focuses it, as incident beam to a spot on sample, reflected electromagnetic radiation from said spot on said sample being collected by said at least one concave spherical mirror, which reflectively directs it to reflect from said convex spherical mirror and emerge as output beam;
said input and output aberation correction system means being positioned so that both input and output beams pass therethrough.

Another description of a present invention system provides that it is a spectroscopic ellipsometer sequentially comprising:
a) a source of a spectroscopic beam electromagnetic radiation;
b) a polarizer element;

in either order elements c and d:
c) optionally a rotating or rotatable compensator element;
d) a reflective optic input system;
e) a sample system;

in either order elements f and g:
f) a reflective optic output system;
g) optionally a rotating or rotatable compensator element;
h) an analyzer element; and
i) a spectroscopic detector system;

at least one of said optional rotating or rotatable compensator elements in c or g being present and oriented so that a spectroscopic electromagnetic beam provided by the source thereof transmits therethrough along its axis of rotation.

Said reflective optic input system, sample system, and said reflective optic output system are comprised in a beam directing system comprising:
a substantially planar mirror;
a convex spherical mirror;
at least one concave spherical mirror; and
aberation correction system means;
such that in use said substantially planar mirror directs a beam electromagnetic radiation to reflect therefrom and proceed as a beam to reflect from said convex spherical mirror, to said at least one concave spherical mirror which focuses it, as incident beam to a spot on sample, reflected electromagnetic radiation from said spot on said sample being collected by said at least one concave spherical mirror, which reflectively directs it to reflect from said convex spherical mirror and emerge as output beam;
said input and output aberation correction system means being positioned so that both input and output beams pass therethrough; and
a detector of electromagnetic radiation;
said system further comprising at least one rotating or rotatable compensator positioned so that said beam of electromagnetic radiation transmits therethrough;

such that in use, said source of electromagnetic radiation provides a beam of electromagnetic radiation to said beam directing system, which in turn causes said beam of electromagnetic radiation to interact with said spot on said sample and then proceed into said detector of electromagnetic radiation, as said rotating or rotable compensator is caused to continuously rotate or step through sequence of descrete positions.

In language similar to that Allowed in Parent U.S. Pat. No. 5,872,630 to Johs et al., the present invention can be described as a spectroscopic ellipsometer system comprising a source of a polychromatic beam of electromagnetic radiation, a polarizer, a stage for supporting a sample system, an analyzer, a dispersive optics and at least one detector system which comprises a multiplicity of detector elements, said spectroscopic ellipsometer system further comprising at least one compensator(s) positioned at a location selected from the group consisting of:
before said stage for supporting a sample system;
after said stage for supporting a sample system; and
both before and after said stage for supporting a sample system;

such that when said spectroscopic ellipsometer system is used to investigate a sample system present on said stage for supporting a sample system at least one of said at least one compensator(s) is caused to continuously rotate while a polychromatic beam of electromagnetic radiation produced by said source of a polychromatic beam of electromagnetic radiation is caused to pass through said polarizer and said at least one compensator(s), said polychromatic beam of electromagnetic radiation being also caused to interact with a sample system on said stage for supporting a sample system, pass through said analyzer and interact with said dispersive optics such that a multiplicity of essentially single wavelengths are caused to simultaneously enter a corresponding multiplicity of detector elements in said at least one detector system;

wherein said spectroscopic ellipsometer system is characterized by:

a beam directing system comprising:
a substantially planar mirror;
a convex spherical mirror;
at least one concave spherical mirror; and
aberation correction system means;
such that in use said substantially planar mirror directs a beam of electromagnetic radiation to reflect therefrom and proceed as a beam to reflect from said convex spherical mirror, to said at least one concave spherical mirror which focuses it, as incident beam to a spot on sample, reflected electromagnetic radiation from said spot on said sample being collected by said at least one concave spherical mirror, which reflectively directs it to reflect from said convex spherical mirror and emerge as output beam;
said input and output aberation correction system means being positioned so that both input and output beams pass therethrough.
In general, a described present invention system can be present in a chamber configured as a selection from the group consisting of:
it comprises at least one chamber region in which is present polarization state generator comprising component(s) prior to said sample system, said sample system, and polarization state detector comprising component(s) after said sample system;
it comprises at least three chamber regions, in one of which is present polarization state generator comprising component(s) prior to said sample system, in the second of which is present the sample system and in the third of which is present polarization state detector comprising component(s) after said sample system;

it comprises at least two chamber regions, in one of which is present polarization state generator comprising component(s) prior to said sample system and said sample system, and in the second of which is present polarization state detector comprising component(s) after said sample system;

it comprises at least two chamber regions, in one of which is present polarization state generator comprising component(s) prior to said sample system, and in the second of which is present polarization state detector comprising component(s) after said sample system and said sample system.

Continuing, while the present invention can utilize essentially any Compensator such as:

Berek-type with optical axis essentially perpendicular to a surface thereof;

non-Berek-type with an optical axis essentially parallel to a surface thereof;

zero-order wave plate;

zero-order waveplate constructed from two multiple order waveplates;

a sequential plurality of zero-order waveplates, each constructed each from a plurality of multiple order waveplates;

rhomb;

polymer;

achromatic crystal; and pseudo-achromatic.

preferred embodiments of the present invention provides that at least one of said at least one compensator(s), which is mounted to allow continuous rotation or step-wise rotation about the locus of a beam of electromagentic radiation caused to pass therethrough, be selected from the group consisting of:

a single element compensator;

a multiple element compensator;

a compensator system comprised of at least two per se. zero-order waveplates (MOA) and (MOB), said per se. zero-order waveplates (MOA) and (MOB) having their respective fast axes rotated to a position offset from zero or ninety degrees with respect to one another, with a nominal value being forty-five degrees;

a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position at a nominal forty-five degrees to the fast axes (FAA1) and (FAB1), respectively, of the multiple order waveplates (MOA1) and (MOB1) in said first effective zero-order waveplate (ZO1);

a compensator system comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position away from zero or ninety degrees with respect to the fast axes (FAA1) and (FAB1), respectively, of the multiple order waveplates (MOA1) and (MOB1) in said first effective zero-order waveplate (ZO1);

a compensator system comprised of at least one zero-order waveplate, ((MOA) or (MOB)), and at least one effective zero-order waveplate, ((ZO2) or (ZO1) respectively), said effective zero-order wave plate, ((ZO2) or (ZO1)), being comprised of two multiple order waveplates which are combined with the fast axes thereof oriented at a nominal ninety degrees to one another, the fast axes of the multiple order waveplates in said effective zero-order wave plate, ((ZO2) or (ZO1)), being rotated to a position away from zero or ninety degrees with respect to the fast axis of the zero-order waveplate, ((MOA) or (MOB));

where the identifiers are shown in FIGS. 3e-3i.

Additional compensator systems, previously disclosed in patent application Ser. No. 08/997,311, (now U.S. Pat. No. 5,946,098), and CIP's therefrom, which are specifically within the scope of the invention and can be included in the selection group are:

a compensator system comprised of a first triangular shaped element, which as viewed in side elevation presents with first and second sides which project to the left and right and downward from an upper point, which first triangular shaped element first and second sides have reflective outer surfaces; said retarder system further comprising a second triangular shaped element which as viewed in side elevation presents with first and second sides which project to the left and right and downward from an upper point, said second triangular shaped element being made of sample which provides reflective interfaces on first and second sides inside thereof; said second triangular shaped element being oriented with respect to the first triangular shaped element such that the upper point of said second triangular shaped element is oriented essentially vertically directly above the upper point of said first triangular shaped element; such that in use an input electromagnetic beam of radiation caused to approach one of said first and second sides of said first triangular shaped element along an essentially horizontally oriented locus, is caused to externally reflect from an outer surface thereof and travel along a locus which is essentially upwardly vertically oriented, then enter said second triangular shaped element and essentially totally internally reflect from one of said first and second sides thereof, then proceed along an essentially horizontal locus and essentially totally internally reflect from the other of said first and second sides and proceed along an essentially downward vertically oriented locus, then externally reflect from the other of said first and second sides of said first triangular shaped elements and proceed along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of, as viewed in upright side elevation, first and second orientation adjustable mirrored elements which each have reflective surfaces; said compensator/retarder system further comprising a third element which, as viewed in upright side elevation, presents with first and second sides which project to the left and right and downward from an upper point, said third element being made of sample which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation even when said compensator/retarder is caused to rotate; with a result being that retardation is entered between orthogonal components of said input electromagnetic beam of radiation;

a compensator system comprised of a parallelogram shaped element which, as viewed in side elevation, has top and bottom sides parallel to one another, both said top and bottom sides being oriented essentially horizontally, said retarder system also having right and left sides parallel to one another, both said right and left sides being oriented at an angle to horizontal, said retarder being made of a sample with an index of refraction greater than that of a surrounding ambient; such that in use an input beam of electromagnetic radiation caused to enter a side of said retarder selected from the group consisting of: (right and left), along an essentially horizontally oriented locus, is caused to diffracted inside said retarder system and follow a locus which causes it to essentially totally internally reflect from internal interfaces of both said top and bottom sides, and emerge from said retarder system from a side selected from the group consisting of (left and right respectively), along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of first and second triangular shaped elements, said first triangular shaped element, as viewed in side elevation, presenting with first and second sides which project to the left and right and downward from an upper point, said first triangular shaped element further comprising a third side which is oriented essentially horizontally and which is continuous with, and present below said first and second sides; and said second triangular shaped element, as viewed in side elevation, presenting with first and second sides which project to the left and right and upward from an upper point, said second triangular shaped element further comprising a third side which is oriented essentially horizontally and which is continuous with, and present above said first and second sides; said first and second triangular shaped elements being positioned so that a rightmost side of one of said first and second triangular shaped elements is in contact with a leftmost side of the other of said first and second triangular shaped elements over at least a portion of the lengths thereof; said first and second triangular shaped elements each being made of sample with an index of refraction greater than that of a surrounding ambient; such that in use an input beam of electromagnetic radiation caused to enter a side of a triangular shaped element selected from the group consisting of: (first and second), not in contact with said other triangular shape element, is caused to diffracted inside said retarder and follow a locus which causes it to essentially totally internally reflect from internal interfaces of said third sides of each of said first and second triangular shaped elements, and emerge from a side of said triangular shaped element selected from the group consisting of: (second and first), not in contact with said other triangular shape element, along an essentially horizontally oriented locus which is undeviated and undisplaced from the essentially horizontally oriented locus of said input beam of essentially horizontally oriented electromagnetic radiation even when said retarder is caused to rotate; with a result being that retardation is entered between orthogonal components of said input electromagnetic beam of radiation;

a compensator system comprised of a triangular shaped element, which as viewed in side elevation presents with first and second sides which project to the left and right and downward from an upper point, said retarder system further comprising a third side which is oriented essentially horizontally and which is continuous with, and present below said first and second sides; said retarder system being made of a sample with an index of refraction greater than that of a surrounding ambient; such that in use a an input beam of electromagnetic radiation caused to enter a side of said retarder system selected from the group consisting of: (first and second), along an essentially horizontally oriented locus, is caused to diffracted inside said retarder system and follow a locus which causes it to essentially totally internally reflect from internal interface of said third sides, and emerge from said retarder from a side selected from the group consisting of (second and first respectively), along an essentially horizontally oriented locus which is undeviated and undisplaced from the essentially horizontally oriented locus of said input beam of essentially horizontally oriented electromagnetic radiation even when said retarder system is caused to rotate; with a result being that retardation is entered between orthogonal components of said input electromagnetic beam of radiation; and a compensator system comprised of first and second Berek-type retarders which each have an optical axes essentially perpendicular to a surface thereof, each of which first and second Berek-type retarders has a fast axis, said fast axes in said first and second Berek-type retarders being oriented in an orientation selected from the group consisting of: (parallel to one another and other than parallel to one another); said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation even when said retarder system is caused to rotate; with a result being that retardation is entered between orthogonal components of said input electromagnetic beam of radiation;

a compensator system comprised of first and second Berek-type retarders which each have an optical axes essentially perpendicular to a surface thereof, each of which first and second Berek-type retarders has a fast axis, said fast axes in said first and second Berek-type retarders being oriented other than parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation, said compensator system further comprising third and forth Berek-type retarders which each have an optical axes essentially perpendicular to a surface thereof, each of which third and forth Berek-type retarders has a fast axis, said fast axes in said third and forth Berek-type retarders being oriented other than parallel to one another, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation;

a compensator system comprised of first, second, third and forth Berek-type retarders which each have an optical axes essentially perpendicular to a surface thereof, each of which first and second Berek-type retarders has a fast axis, said fast axes in said first and second Berek-type retarders being oriented essentially parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation; each of which third and forth Berek-type retarders has a fast axis, said fast axes in said third and forth Berek-type retarders being oriented essentially parallel to one another but other than parallel to the fast axes of said first and second Berek-type retarders, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation even when said retarder system is caused to rotate; with a result being that retardation is entered between orthogonal components of said input electromagnetic beam of radiation;

said compensator causing essentially no deviation or displacement in a polychromatic beam of electromagnetic radiation caused to pass therethrough while caused to rotate.

It is to be appreciated that the present invention can apply Compensator(s) in a system which causes continuous rotation thereof during data acquisition, or steps a compensator through a series of discrete rotational positions, and holds it stationary while obtaining data. Further, while not required, the present invention benefits from Compensator(s) designed to provide relatively constant, achromatic Polarization State Modification effects over a Spectroscopic range of wavelengths.

As another previously disclosed, (in Co-Pending application Ser. No. 09/517,125), non-limiting example, the spectroscopic ellipsometer system can provide at least one means for discretely, sequentially, modifying a polarization state of a beam of electromagnetic radiation provided by said source of polychromatic electromagnetic radiation through a plurality of polarization states, can comprise an essentially circular "wheel" element with a plurality of discrete polarization state modifier elements mounted thereupon, on the perimeter thereof, and projecting perpendicularly to a surface of said essentially circular "wheel". The essentially circular "wheel" element further comprises a means for causing rotation about a normal to said surface thereof, such that in use said essentially circular "wheel" element is caused to rotate to position a discrete polarization state modifier element such that the beam of electromagnetic radiation, provided by said source of polychromatic electromagnetic radiation, passes therethrough.

Further, as the polarizer in the present invention spectroscopic ellipsometer system remains essentially fixed in position during data acquisition, it is noted that it is preferable that a source of electromagnetic radiation, and/or a present Polarizer or Polarization State Generator be positioned or configured so as to pass predominately "S" Polarized electromagnetic radiation, as referenced to said beam combining system. The reason for this is that the split between "S" polarization transmission and reflection components is less, as a function of wavelength and electromagnetic beam angle-of-incidence to said beam combining means, when compared to that of the "P" components. The "P" component is far more affected, particularly around a Brewster angle condition, hence, where an "S" component, with reference to a beam combining system, is utilized, it is to be appreciated that variation in intensity of transmitted and reflected beams of electromagnetic radiation output from the beam combining system, as functions of wavelength and the angles of incidence of beams of electromagnetic radiation from sources of said transmitted and reflected beams of electromagnetic radiation, is minimized, as compared to variation which occurs in "P" components.

It is noted that the polarizer and analyzer thereof, which are essentially fixed in position during data acquisition, are not necessarily absolutely fixed in position. Said polarizer and analyzer are preferably what is properly termed "Rotatable". That is they can be rotated to various positions by a user between data acquisitions, but they are not caused to be Rotating while data is being acquired. (Typical positioning of analyzer and polarizer azimuthal angles are plus or minus forty-five (+/−45) degrees)).

It is also noted that operation of the present invention can be generally improved by improving the quality of the electromagnetic radiation.

A first approach is to provide a back reflector behind a source of electromagnetic radiation, which serves to direct electromagentic radiation which exits the source in a useful direction.

Another approach is to provide a reflecting means in the pathway of the electromagnetic beam, upon which reflecting means is a coating which emphasises reflection of the UV and particularly at 193 nm. An example of such a coating on a reflective means is 600 Angstroms of Silicon Dioxide atop Silicon. This approach enables setting "gain" providing means at higher levels to emphasize UV signals, while not over amplifying, and even saturating higher intensity wavelengths signals.

Another approach is to coat transmissive elements such as lenses present in the system, to minimize entry and exit losses caused thereby, and improve overall UV transmission therethrough. An example is a single 300 Angstrom layer of $MgF_2$. Multilayer coatings can also be used.

Another approach is to provide a Grating which has characteristics that emphasize UV wavelengths and/or direct a utilized "Order" of wavelengths in a direction which is subject to less influence by the zero and/or other orders.

Further, application of baffling to block access of zero and/or other orders of electromagnetic radiation to detector means can be applied.

Approaches which focus on optical fibers are:

Another approach is to eliminate optical fibers which, while convenient for use directing electromagentic radiation, also serve to attenuate UV wavelength intensity via entry loss and transmission attenuation.

However, if optical fibers are utilized, to reduce UV intensity at fiber entry loss a narrow slit (eg. smaller that the fiber dimension), can be placed at the entry to the fiber.

The following approaches focus on increasing the amount of UV electromagnetic radiation and can be practiced independently or in combination:

Another approach is to utilize a source of electromagnetic radiation which emphasises UV wavelength production.

Various wattage lamps (eg. 35, 75 and 150 can be applied and where necessary can involve application of various indirect heat sink based cooling and produced ozone containment.

Another approach is to, in the case of rotating compensator ellipsometers, reduce the rotation speed of the compensator so that for the same number of rotations more total electromagentic radiation passes therethrough and reaches the detector.

Another approach is to take multiple scans of data to improve signal to noise.

Another approach is to combine the output of multiple pixels in a detector which receive UV radiation.

It is also disclosed that the presently disclosed spectroscopic ellipsometer can be mounted in a Chamber for controlling the ambient. Examples of the Chamber are:
  it comprises at least one chamber region in which is present polarization state generator comprising component(s) prior to said sample system, said sample system, and polarization state detector comprising component(s) after said sample system;
  it comprises at least three chamber regions, in one of which is present polarization state generator comprising component(s) prior to said sample system, in the second of which is present the sample system and in the third of which is present polarization state detector comprising component(s) after said sample system;
  it comprises at least two chamber regions, in one of which is present polarization state generator comprising component(s) prior to said sample system and said sample system, and in the second of which is present polarization state detector comprising component(s) after said sample system;
  it comprises at least two chamber regions, in one of which is present polarization state generator comprising component(s) prior to said sample system, and in the second of which is present polarization state detector comprising component(s) after said sample system and said sample system.

It is believed that the present invention spectroscopic ellipsometer system combination comprising:
  polarizer and analyzer, (which are both fixed in position during data acquisition); and
  at least one rotating or stepwise rotatable compensator means for discretely, sequentially, modifying a polarization state of a beam of electromagnetic radiation provided by said source of polychromatic electromagnetic radiation through a plurality of polarization states, said means being present at least one location selected from the group consisting of:
    between said polarizer and said stage for supporting a sample system; and
    between said stage for supporting a sample system and said analyzer;
  said at least one rotating or stepwise rotatable compensator means for discretely, sequentially, modifying a polarization state of a beam of electromagnetic radiation provided by said source of polychromatic electromagnetic radiation through a plurality of polarization states, and said at least one multiple element lens being positioned so that said beam of electromagnetic radiation transmits therethrough in use;
  wherein said system further comprises a beam directing system comprising:
    a substantially planar mirror;
    a convex spherical mirror;
    at least one concave spherical mirror;
  aberation correction system means;
  such that in use said substantially planar mirror directs a beam of electromagnetic radiation to reflect therefrom and proceed as a beam to reflect from said convex spherical mirror, to said at least one concave spherical mirror which focuses it, as incident beam to a spot on sample, reflected electromagnetic radiation from said spot on said sample being collected by said at least one concave spherical mirror, which reflectively directs it to reflect from said convex spherical mirror and emerge as output beam;
  said input and output aberation correction system means being positioned so that both input and output beams pass therethrough;

is Patentably distinct over all prior art other than patents which are co-owned by the J. A. Woollam Co. Inc. from which this application Continues-In-Part or from which this application otherwise has priority benefit.

The present invention will be better understood by reference to the Detailed Description Section of this Specification, in combination with the Drawings.

SUMMARY

It is therefore a primary purpose and/or objective of the present invention to disclose a combination of:
  spectroscopic ellipsometer and combined spectroscopic reflectometer/ellipsometer systems, which present invention system includes, in the spectroscopic ellipsometer portion thereof, provision of polarizer and analyzer elements which are fixed in position during data acquisition procedures, and at least one continuously rotating or stepwise rotatable compensator means for imposing a plurality of sequentially discrete, rather than continuously varying, polarization states onto a beam of electromagnetic radiation caused to be present in said spectroscopic ellipsometer system; said system further comprising menas for providing electromagnetic radiation to a spot on a sample at a multiplicity of angles of incidence, and after reflection of said beam therefrom into a detector, said system including at least one spherical mirror, and a refractive means for correcting aberation.

It is another purpose and/or objective of the disclosed invention to teach applying a plurality of duplicate systems for providing electromagnetic radiation to a spot on a sample, sequentially at a multiplicity of angles of incidence, and after reflection of said beam therefrom into a detector, said system including a plurality of spherical mirrors, and a refractive means for correcting aberation, each oriented at some offset angle with respect to the other of said plurality of duplicate systems.

It is another purpose and/or objective yet of the presently disclosed invention to teach containing a spectroscopic ellipsometer in an environmental chamber.

Other purposes and/or objectives will become clear from a reading of the Specification and Claims.

BRIEF DESCRIPTION OF THE DRAWINGS

FIG. 3*a* shows a frontal perspective view of a discrete state compensator system comprising a wheel with five discrete polarizer elements mounted thereupon.

FIG. 3*b* shows a side elevational view of a discrete state compensator system, as in FIG. 3*a*, oriented so that an electromagnetic beam passing through one of the discrete polarizer five elements.

FIG. 3*c* shows a front elevational view of a discrete state compensator system, with five laterally slideably mounted discrete elements mounted therein.

FIG. 3*d* shows a front elevational view of a discrete state compensator system, with five laterally rotatably mounted discrete elements mounted therein.

FIGS. 3j1-3p show additional functional construction of compensator systems which are within the scope of the present invention.

FIG. 11 shows an enlarged partial view of the system shown in FIG. 8, and demonstrates that substantially Planar Mirror (4) is can be caused to move into a plurality of horizontally located positions, the effect said positioning being to control the angle-of-incidence at which the beam eventually arrives at the Sample (SS).

FIG. 12 is included to show that a plurality of duplicate systems can be oriented so as to direct beams of electromagnetic radiation (3) (3') produced thereby toward the Convex Spherical Mirror (10) thereof at offsets with respect to one another as viewed from above the Convex Spherical Mirror (10).

DETAILED DESCRIPTION

FIGS. 1-6 show sample previously disclosed in Co-Pending application Ser. No. 09/517,125. More specifically, it is noted that FIGS. 3e-3p show demonstrative designs for substantially achromatic Transmissive Compensators. The disclosure pertaining to FIGS. 1-6 is to provide a basis for understanding the improvements thereto to arrive at the present invention.

Figure 1:
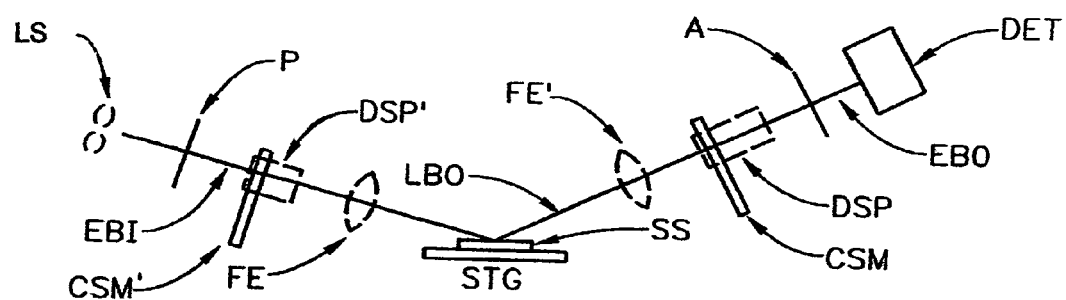
FIG. 1 shows a present invention spectroscopic ellipsometer system configuration.

Turning now to FIG. 1, there is shown a demonstrative spectroscopic ellipsometer system configuration. Shown are a source of polychromatic electromagnetic radiation (LS), (eg. a quartz-halogen-lamp), a polarizer (P) a stage for supporting a sample system (STG) with a sample system (SS) present thereupon, a Compensator means (CMP) for continuously or discretely, sequentially, modifying a polarization state of a beam of electromagnetic radiation provided by said source of polychromatic electromagnetic radiation through a plurality of polarization states by passage therethrough, an analyzer (A), and a detector system (DET). (Note preferred detector systems are spectroscopic, (multi-element), such as Bucket Brigade, Diode and CCD arrays and that "off-the-shelf" spectrometer systems such as manufactured by Zeiss can also be applied). Shown also are ellipsometer electromagnetic beam in (EBI) and ellipsometer electromagnetic beam out (EBO). It is noted that said Compensator means (CMP) for continuously or discretely, sequentially, modifying a polarization state of a beam of electromagnetic radiation, while shown as present between said stage (STG) for supporting a sample system (SS) and said analyzer (A), can generally be present as (CMP') between said polarizer (P) and said stage (STG) for supporting a sample system (SS), and/or as (CMP) between said stage (STG) for supporting a sample system and said analyzer (A).

It is noted that the combination of elements (LS), (P), and (CMP') is sometimes described as a Polarization State Generation System, and the combination of elements (CMP) (A) and (DET) is sometimes described as a Polarization State Detection System. Also, it is to be understood that the Polarization State Detection System could be rotated so as to position the Detector (DET) to detect electromagnetic radiation transmitted through the Sample (SS), and remain within the scope of the invention.

Figure 2:
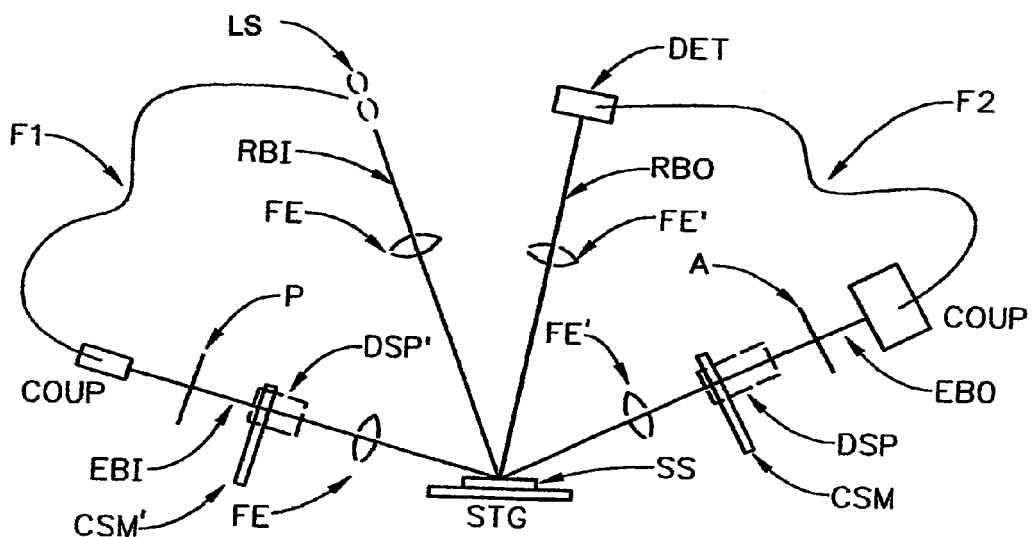
FIG. 2 shows a combined present invention spectroscopic reflectometer/ellipsometer system.

FIG. 2 shows a combined spectroscopic reflectometer/ellipsometer system wherein the source of polychromatic electromagnetic radiation (LS), and detector (DET) system are common to both, and wherein the spectroscopic ellipsometer system is shown as being provided input and output electromagnetic beam access via fiber optics (F1) and (F2). Shown are near-normal orientation reflectometer electromagnetic beam in (RBI) and reflectometer electromagnetic beam out (RBO), as well as sample system (SS) specific near Brewster condition ellipsometer electromagnetic beam in (EBI) and ellipsometer electromagnetic beam out (EBO). While not shown, it is noted that the source of polychromatic electromagnetic radiation (LS), and detector (DET) system can be located distal from both the reflectometer and ellipsometer portions of the combined spectroscopic reflectometer/ellipsometer system, with fiber optics being present to interface to the reflectometer portion as well.

In both FIGS. 1 and 2, there can optionally be other (eg. focusing elements ((FE) (FE')), present on one or both sides of the sample system (SS), as shown in dashed lines. Said other elements appear ellipsometrically indistinguishable with polarization state modifiers during use. Also shown in FIGS. 1 & 2 are Compensator Rotating or Stepping Means (CSM) (CSM') for use in continuously rotating or stepwise rotating compensator (CMP) and/or (CMP') or operating means as shown in FIGS. 3a-3c.

FIG. 3a shows a frontal perspective view of a discrete state compensator (CMP) comprising an essentially circular "wheel" element (WE) with five discrete polarization state modifiers elements (A) (B) (C) (D) and (E) mounted thereupon on the perimeter thereof, such that said and projecting discrete polarization state modifier elements (A) (B) (C) (D) and (E) project perpendicularly to a surface thereof. FIG. 3b shows a side elevational view of a discrete state compensator, as in FIG. 3a, oriented so that an electromagnetic beam (EM) passing through one (C) of the five discrete polarization state modifiers (A) (B) (C) (D) and (E) elements. Note that discrete compensator elements (A) and (B) are located behind discrete compensator elements (E) and (D) respectively. Also note that if the essentially circular "wheel" element (WE) is caused to rotate about the pivot rod (PR) which projects from a lower surface of said essentially circular "wheel" element, each of the various five discrete compensator (A) (B) (C) (D) and (E) elements can be rotated into the position in which is shown discrete polarizer element (C). FIG. 3c shows a front elevational view of a discrete state compensator with five laterally slideably mounted discrete polarizer (A) (B) (C) (D) and (E) elements mounted on a slider element (SE) which is mounted in a guide providing element (GE) therein. Sliding the slider element (SE) to the right or left serves to position each of the five discrete compensator (A) (B) (C) (D) and (E) elements in a position at which an electromagnetic beam of radiation can be caused to be present. (Note more or less than five discrete compensator elements can be present).

Figure 3E:
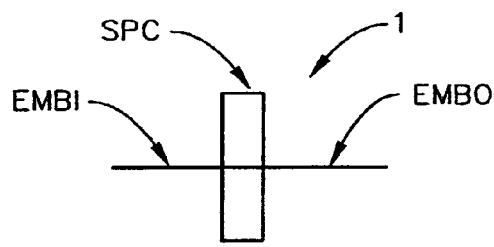
FIGS. 3e-3i demonstrate functional construction of preferred present invention compensator systems.
Figure 3F:
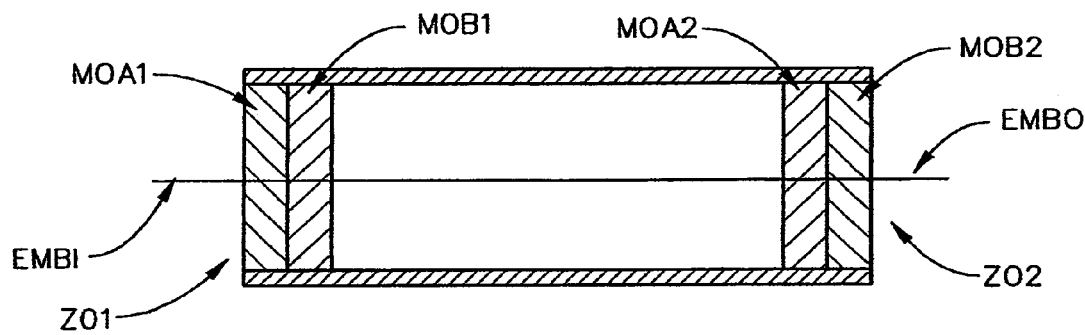
Figure 4:
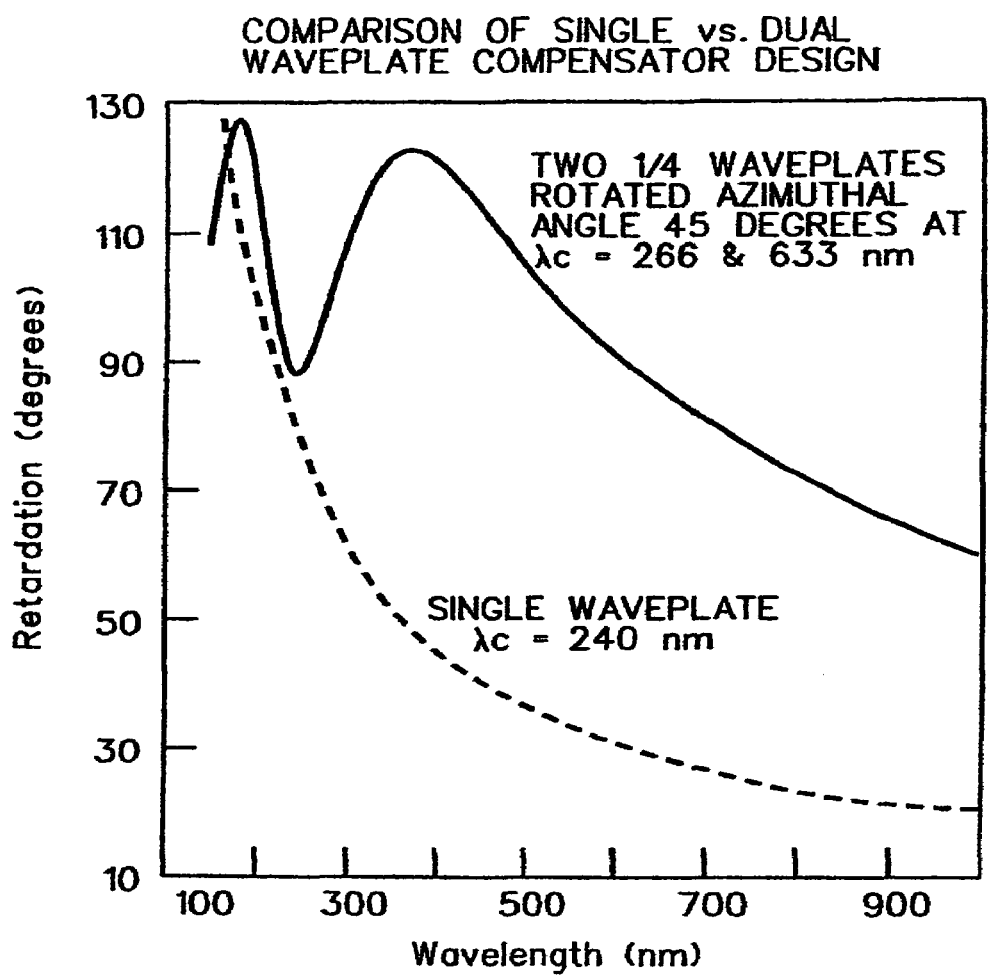
FIGS. 4-6 show Psuedo-Achromatic characteristics achievable by FIG. 3f Compensator design.
Figure 5:
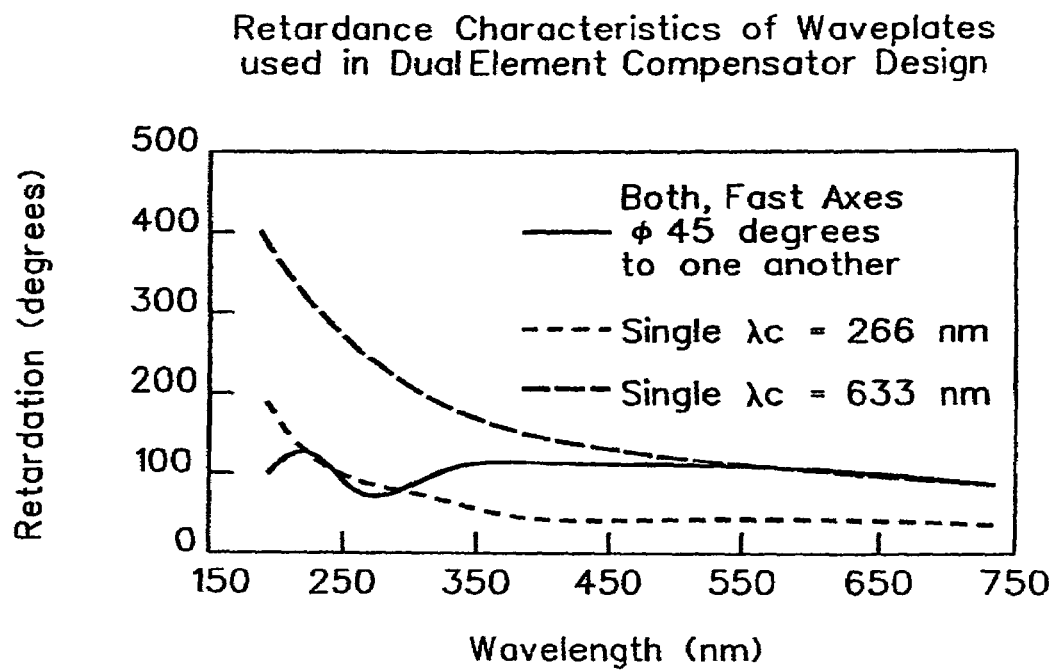
Figure 6:
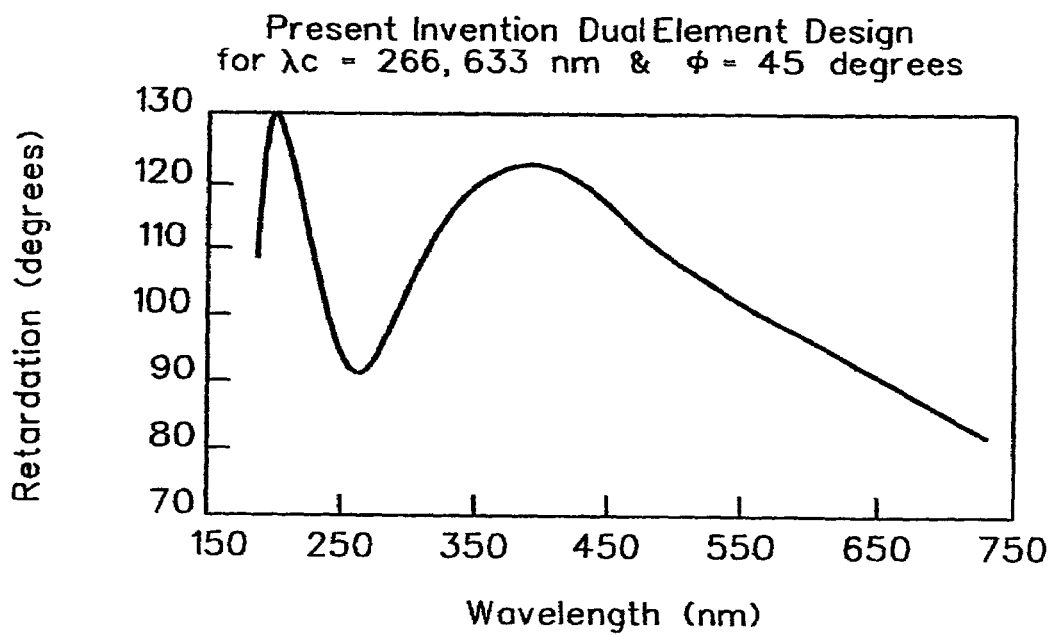

The embodiments in FIGS. 3a-3c have been found to be difficult to practice, however, and it has been determined that a better approach is to utilize transmissive rotatable compensator means to provide the discrete polarization state changes. FIGS. 3e, 3f, 3g, 3h and 3i demonstrate that at least one Compensator can be applied as (CMP) or (CMP'') in FIGS. 1 and 2, which at least one Compensator (CMP) and/or (CMP''), is, in use, rotated about the locus of the electromagnetic beam (EBI) or (EBO), by Compensator Rotation Stepping Means (CSM') and/or (CSM). That is, the presently disclosed invention then comprises a Discrete Polarization State Spectroscopic Ellipsometer System, with the clarification being that the Discrete Polarization State effecting means (CMP) and/or (CMP') is preferably a Rotatable Compensator, which during use is continuously rotated or stepped through a plurality of discrete rotation angles, and then held motionless during data acquisition. While not limiting, a utility providing specific embodiment applies Psuedo-Achromatic Rotatable Compensators. (Note, FIGS. 4-6 show various Psuedo-Achromatic Retardation vs. Wavelength characteristics possible utilizing multiple element compensators, as shown in FIG. 3f).

It is noted that FIG. 3d shows a perspective elevational view of a discrete state compensator system, with six laterally rotatably mounted discrete elements (A) (B) (C) (D) (E) (F) mounted therein. Rotation about axis (PR) places them into the path of Beam (EMBI).

Further, essentially any Compensator which can be placed into a beam of electromagnetic radiation can be applied, such as those disclosed in claim 9 of U.S. Pat. No. 5,872,630, (which 630 patent is incorporated by reference hereinto):
  Berek-type;
  In-Plane Non-Berek-type;
  Zero Order;
  Zero Order comprising a plurality of plates;
  Rhomb;
  Polymer;
  Achromatic Crystal; and
  Psuedo-Achromatic.

Figure 3G:
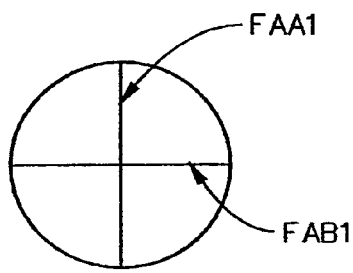
Figure 3H:
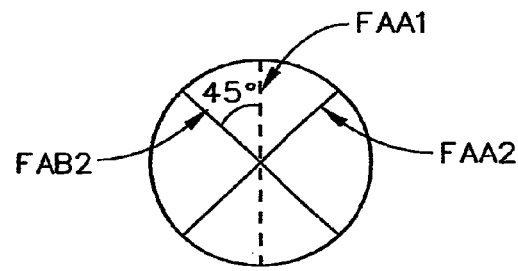
Figure 3I:
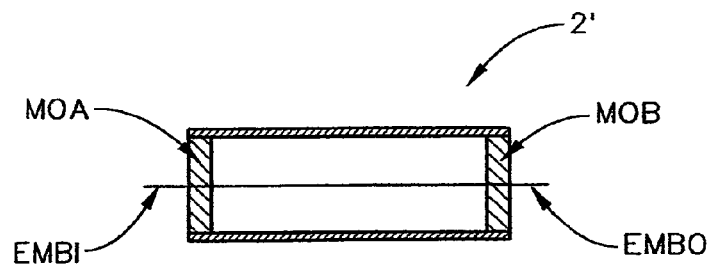

FIGS. 3e, 3f, 3g, 3h and 3i demonstrate functional construction of preferred present invention compensator systems. FIG. 3e simply exemplifies that a single plate (SPC) compensator (1) can be applied. FIG. 3f demonstrates construction of a compensator (2) from first (Zo1) and second (ZO2) effectively Zero-Order, (eg. Quartz or Bicrystalline Cadmium Sulfide or Bicrystalline Cadmium Selenide), Waveplates, each of which effective Zero-Order Waveplates (ZO1) & (ZO2) is shown to be constructed from two Multiple Order waveplates, (ie. (MOA1) & (MOB1) and (MOA2) & (MOB2), respectively). The fast axes (FAA2) & (FAB2) of said second effective Zero-Order Waveplate (ZO2) are oriented away from zero or ninety degrees, (eg. in a range around a nominal forty-five degrees such as between forty and fifty degrees), with respect to the fast axes (FAA1) & (FAB1) of said first effective Zero-Order Waveplate (ZO1). In particular FIG. 14b is a cross-sectional side view of a present invention preferred compensator (PC) constructed from a first effective zero-order plate (ZO1) which is constructed from two multiple order plates (MOA1) and (MOB1), and a second effective zero-order plate (ZO2) which is constructed from two multiple order plates (MOA2) and (MOB2). An entered electromagnetic beam (EMBI) emerges as electromagnetic beam (EMBO) with a retardation entered between orthogonal components thereof with a Retardation vs. Wavelength. FIGS. 3g and 3h are views looking into the left and right ends of the preferred present invention Compensator (PC) as shown in FIG. 3f, and show that the Fast Axes (FAA2) and (FAB2) of the second effective Zero-Order Waveplate (ZO2) are rotated away from zero or ninety degrees and are ideally oriented at forty-five degrees, with respect to the Fast Axes (FAA1) & (FAB1) of the first effective Zero-Order Waveplate (Zo1). (Note that the fast axis (FAA1) of the first effective Zero-Order Waveplate (Zo1) is shown as a dashed line in FIG. 3h, for reference). FIG. 3i demonstrates functional construction of another preferred compensator (2') which is constructed from two per se. single plate Zero-Order Waveplates (MOA) and (MOB), which are typically made of samples such as mica or polymer.

(It is specifically to be understood that a present invention compensator system can be comprised of at least one Zero-Order waveplate and at least one effectively Zero-Order waveplate in combination, as well as combinations comprised of two actual Zero-Order waveplates or two effectively Zero-Order waveplates).

FIGS. 3j1-3p demonstrate additional compensators which can be applied in the present invention.

FIG. 3j1 shows that the first additional present invention retarder system (3) comprises a first triangular shaped element (P1), which as viewed in side elevation presents with first (OS1) and second (OS2) sides which project to the left and right and downward from an upper point (UP1). Said first triangular shaped element (P1) first (OS1) and second (OS2) sides have reflective outer surfaces. Said retarder system (3) further comprises a second triangular shaped element (P2) which as viewed in side elevation presents with first (IS1) and second (IS2) sides which project to the left and right and downward from an upper point (UP2), said second triangular shaped element (P2) being made of sample which provides internally reflective, phase delay introducing, interfaces on first (IS1) and second (IS2) sides inside thereof. Said second triangular shaped element (P2) is oriented with respect to the first triangular shaped element (P1) such that the upper point (UP2) of said second triangular shaped element (P2) is oriented essentially vertically directly above the upper point (UP1) of said first triangular shaped element (P1). In use an input electromagnetic beam of radiation (LB) caused to approach said first (OS1) side of said first triangular shaped element (P1) along an essentially horizontally oriented locus, is shown as being caused to externally reflect from an outer surface thereof and travel along as electromagnetic beam of radiation (R1) which is essentially upwardly vertically oriented. Next said electromagnetic beam of radiation (R1) is caused to enter said second triangular shaped element (P2) and essentially totally internally reflect from said first (IS1) side thereof, then proceed along an essentially horizontal locus and essentially totally internally reflect from the second (IS2) side thereof and proceed along an essentially downward vertically oriented electromagnetic beam of radiation (R3). This is followed by an external reflection from an outer surface of said second side (OS2) of said first triangular shaped element (P1) such that said electromagnetic beam (LB') of radiation proceeds along an essentially horizontally oriented locus, undeviated and undisplaced from the essentially horizontally oriented locus of said input beam (LB) of essentially horizontally oriented electromagnetic radiation. This is the case even when said retarder system (3) is caused to rotate. The result of said described retarder system (3) application being that retardation is entered between orthogonal components of said input electromagnetic beam of radiation (LB). Further, said first (P1) and second (P2) triangular shaped elements are typically right triangles in side elevation as shown in FIG. 3j1, and the outer surfaces of first (OS1) and second (OS2) sides are typically, but not necessarily, made reflective by the presence of a coating of metal thereupon. A coating of metal serves assure a high reflectance and good electromagnetic beam radiation intensity throughput. Also, assuming accurately manufactured right angle first (P1) and second (P2) triangular shaped elements are utilized, this compensator design provides inherent compensation of both angular and translational misalignments of the input light beam (LB). As well, the total retardence provided is compensated for angular misalignments of the input electromagnetic radiation beam. That is, if the input electromagnetic radiation beam (LB) is not aligned so as to form an angle of incidence of forty-five (45) degrees with the first outer surface (OS1), the reflected electromagnetic beam (R1) will internally reflect at the first internal surface (IS1) of the second triangular shaped element (P2) at a larger (smaller) angle than would be the case if said angle of incidence were forty-five (45) degrees. This effect, however, is directly compensated by a smaller (larger) angle of incidence of electromagnetic beam (R2) where it internally reflects from inner surface (IS2) of the second triangular shaped element (P2). As another comment it is to be understood that because of the oblique angles of incidence of the reflections from the outer surfaces (OS1) and (OS2) of the first triangular shaped element (P1) a polarimeter/ellipsometer in which said compensator (3) is present will require calibration to characterize the PSI-like component thereof.

FIG. 3j2 shows a variation (3') on FIG. 3j1, wherein the first triangular shaped element is replaced by two rotatable reflecting means, identified as (OS1') and (OS2'). This modification allows user adjustment so that the locus of an entering electromagentic beam (LB') exits undeviated and undisplaced from an entering electromagentic beam (LB).

Figure 3K:
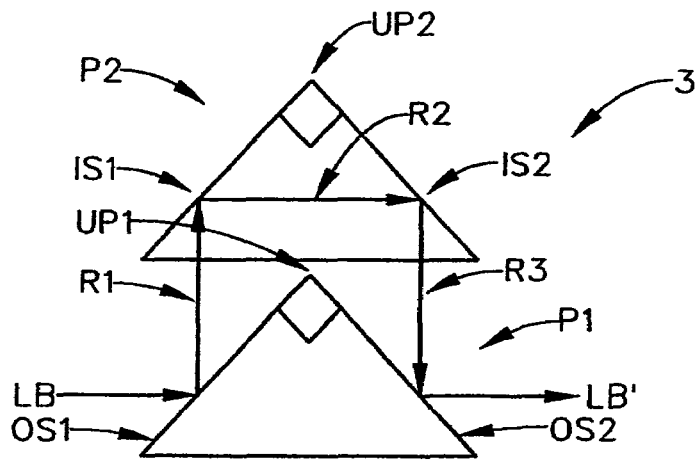
Figure 3K:
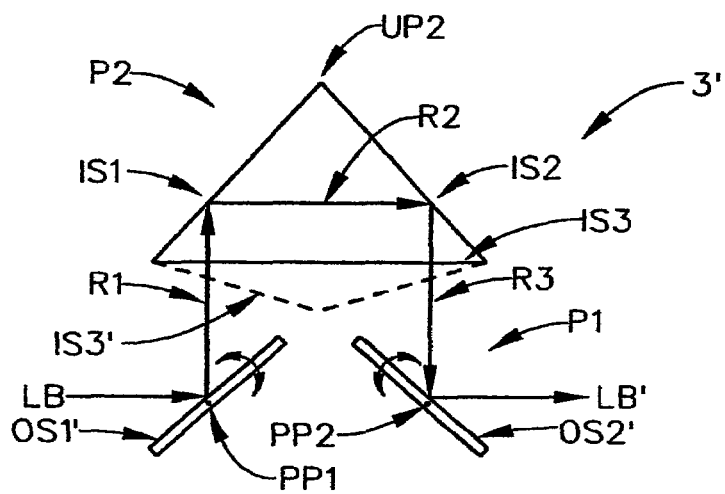
Figure 3K:
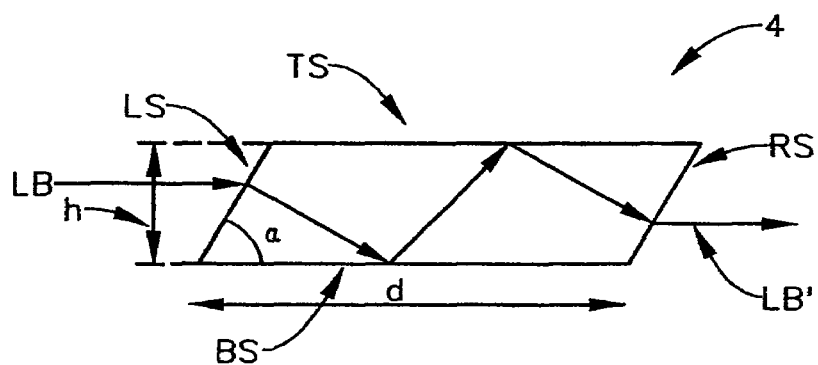
Figure 3L:
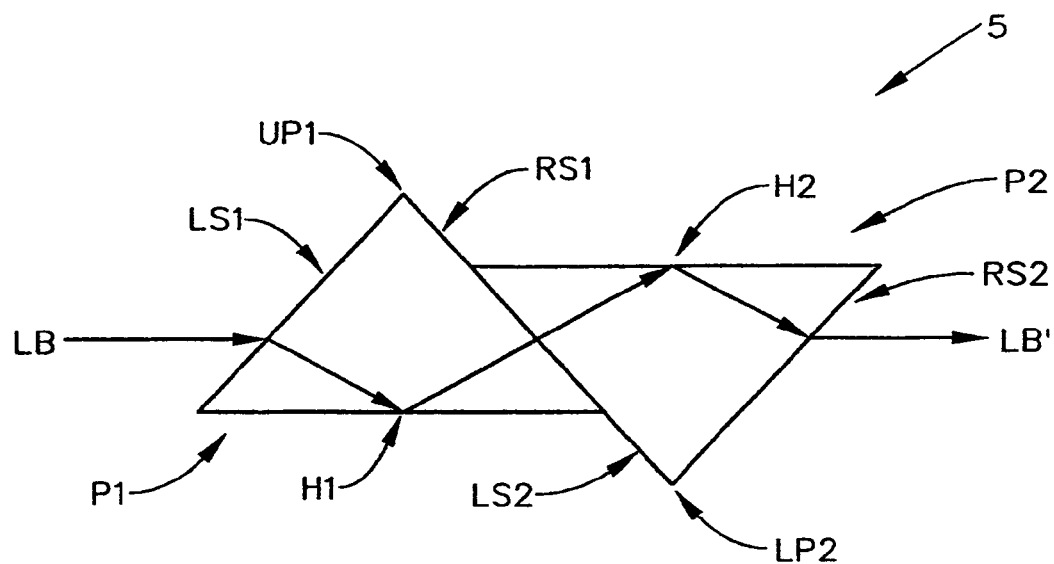

FIG. 3k shows that the second additional present invention retarder system (4) comprises a parallelogram shaped element which, as viewed in side elevation, has top (TS) and bottom sides (BS), each of length (d) parallel to one another, both said top (TS) and bottom (NS) sides being oriented essentially horizontally. Said retarder system (4) also has right (RS) and left (LS) sides parallel to one another, both said right (RS) and left (LS) sides being of length (d/cos(∝)), where alpha (∝) is shown as an angle at which said right (RS) and left (LS) sides project from horizontal. Said retarder system (4) is made of a sample with an index of refraction greater than that of a surrounding ambient. In use an input beam of electromagnetic radiation (LB) caused to enter the left side (LS) of said retarder system (4), along an essentially horizontally oriented locus, is caused to diffracted inside said retarder system (4) and follow a locus which causes it to essentially totally internally reflect from internal interfaces of both said top (TS) and bottom (BS) sides, and emerge from said retarder system (4) as (LB') from the right side (RS) thereof, along an essentially horizontally oriented locus which is undeviated and undisplaced from the essentially horizontally oriented locus of said input beam (LB) of essentially horizontally oriented electromagnetic radiation. This is the case even when said retarder system (4) is caused to rotate. The result of said described retarder system (4) application being that retardation is entered between orthogonal components of said input electromagnetic beam of radiation at said internal reflections from the top (TS) and bottom (BS) surfaces. This retarder system is very robust as it is made of single piece construction. It is noted that adjustment of the angle alpha (∝) in manufacture allows setting the amount of retardation which is provided by the retarder system (4). In addition, coatings can be externally applied to top (TS) and bottom surface (BS) to adjust retardation effected by internal reflection from said top (TS) and bottom (BS) surfaces. A formula which defines the retardation provided thereby being:

FIG. 3l shows that the third additional present invention retarder system (5) comprises first (P1) and second (P2) triangular shaped elements. Said first (P1) triangular shaped element, as viewed in side elevation, presents with first (LS1) and second (RS1) sides which project to the left and right and downward from an upper point (UP1), said first triangular shaped element (P1) further comprising a third side (H1) which is oriented essentially horizontally and which is continuous with, and present below said first (LS1) and second (RS1) sides. Said second triangular shaped element (P2), as viewed in side elevation, presents with first (LS2) and second (RS2) sides which project to the left and right and upward from a lower point (LP2), said second triangular shaped element (P2) further comprising a third side (H2) which is oriented essentially horizontally and which is continuous with, and present above said first (LS2) and second (RS2) sides. Said first (P1) and second (P2) triangular shaped elements being positioned so that a rightmost side (RS1) of said first (P1) triangular shaped element is in contact with a leftmost side (LS2) of said second (P2) triangular shaped element over at least a portion of the lengths thereof. Said first (P1) and second (P2) triangular shaped elements are each made of sample with an index of refraction greater than that of a surrounding ambient. In use an input beam (LB) of electromagnetic radiation caused to enter the left (LS1) side of said first (P1) triangular shaped element and is caused to diffracted inside said retarder system (5) and follow a locus which causes it to essentially totally internally reflect from internal interfaces of said third sides (H1) and (H2) of said first (P1) and second (P2) triangular shaped elements, respectively, and emerge from said right side (RS2) of said second (P2) triangular shaped element as electromagnetic radiation beam (LB') which is oriented along an essentially horizontal locus which is undeviated and undisplaced from the essentially horizontally oriented locus of said input beam (LB) of essentially horizontally oriented electromagnetic radiation. This is the case even when said retarder system (5) is caused to rotate. The result of said described retarder system (5) application being that retardation is entered between orthogonal components of said input electromagnetic beam of radiation (LB). It is noted that as long as the third sides (H1) and (H2) of said first (P1) and second (P2) triangular shaped elements are parallel, the output electromagnetic beam (LB') is undeviated and undisplaced from the input electromagnetic beam (LB) in use. It is noted that The triangular shape elements (P1) and/or (P2) can be made of various samples with various indicies of refraction, and coating(s) can be applied to one or both of the third sides (H1) and (H2) of said first (P1) and second (P2) triangular shaped elements to adjust retardation entered to an electromagnetic beam (LB1).

Figure 3M:
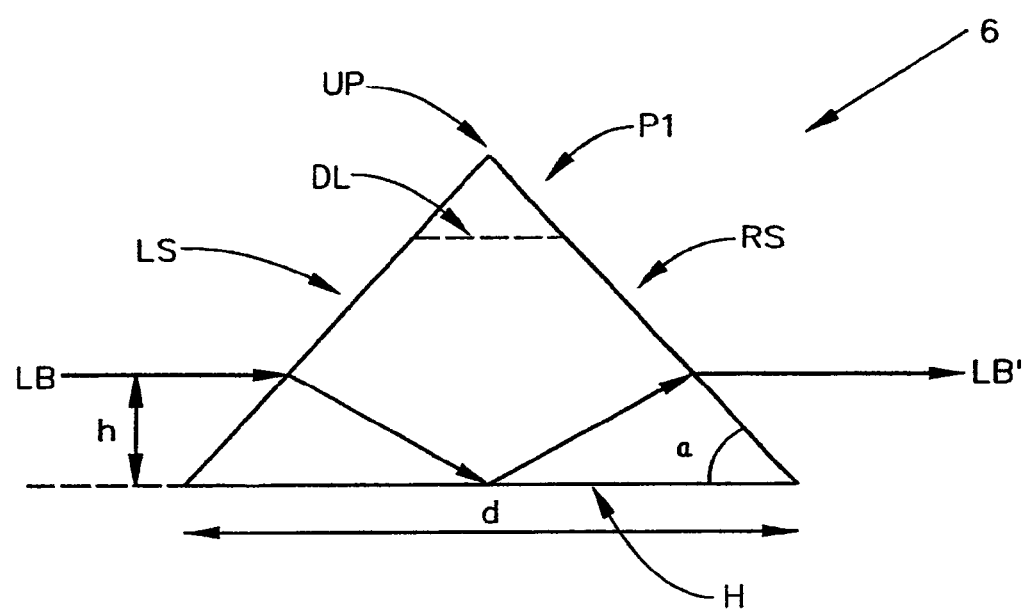

FIG. 3m shows that the forth additional present invention retarder system (6) comprises a triangular shaped element, which as viewed in side elevation presents with first (LS) and second (RS) sides which project to the left and right and downward from an upper point (UP). Said retarder system (6) further comprises a third side (H) which is oriented essentially horizontally and which is continuous with, and present below said first (LS) and second (RS) sides. Said retarder system (6) is made of a sample with an index of refraction greater than that of a surrounding ambient. In use an input beam of electromagnetic radiation (LB) caused to enter the first (LS) side of said retarder system (6) along an essentially horizontally oriented locus, is caused to diffracted inside said retarder system (6) and follow a locus which causes it to essentially totally internally reflect from internal interface of said third (H) side, and emerge from said retarder system (6) from the second (RS) side along an essentially horizontally oriented locus which is undeviated and undisplaced from the essentially horizontally oriented locus of said input beam of essentially horizontally oriented electromagnetic radiation (LB). This is the case even when said retarder system (6) is caused to rotate. The result of said described retarder system (6) application being that retardation is entered between orthogonal components of said input electromagnetic beam of radiation (LB). The FIG. 3*m* retarder system (6) is typically an isosceles prism which is available off-the-shelf with an angle alpha (∝) of forty-five (45) degrees. As long as the input electromagnetic beam (LB) height (h) is chosen in accordance with the formula:

$$d = 2h\left(\frac{1}{\tan(\alpha)} + \tan(\phi)\right), \text{where} \phi = \alpha + \sin^{-1}\left(\frac{\sin(90-\alpha)}{n}\right)$$

in conjunction with the index of refraction (n) of the sample from which the retarder system (6) is made, and the locus of the input electromagnetic radiation beam (LB) is parallel with the third side (H) of said retarder system (6), the output electromagnetic beam (LB') will not be deviated or translated with respect to the input electromagnetic beam (LB). As well, note the dashed line (DL) below the upper point (UP). This indicates that as the region above said dashed line (DL) is not utilized, the portion of said retarder system (6) thereabove can be removed. It is also noted that the input electromagnetic beam (LB) enters and exits the retarder system (6) other than along a normal to a surface thereof, said retarder system is not an ideal retarder with a PSI of forty-five (45) degrees. It is noted that the third side (H) of the retarder system (6) can be coated to change the retardation effects of an internal reflection of an electromagnetic beam of radiation therefrom, and such a coating can have an adverse effect on the nonideal PSI characteristics.

Figure 3P:
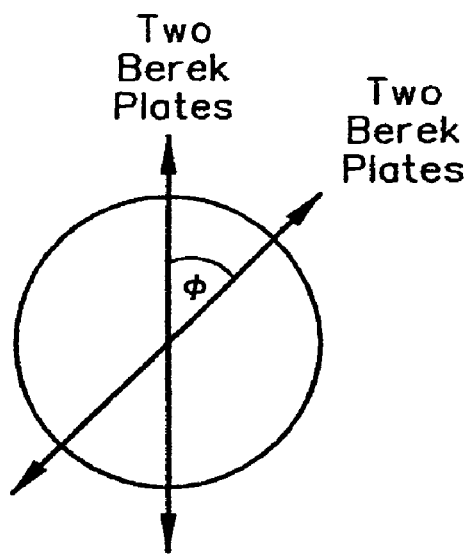
Figure 3P:
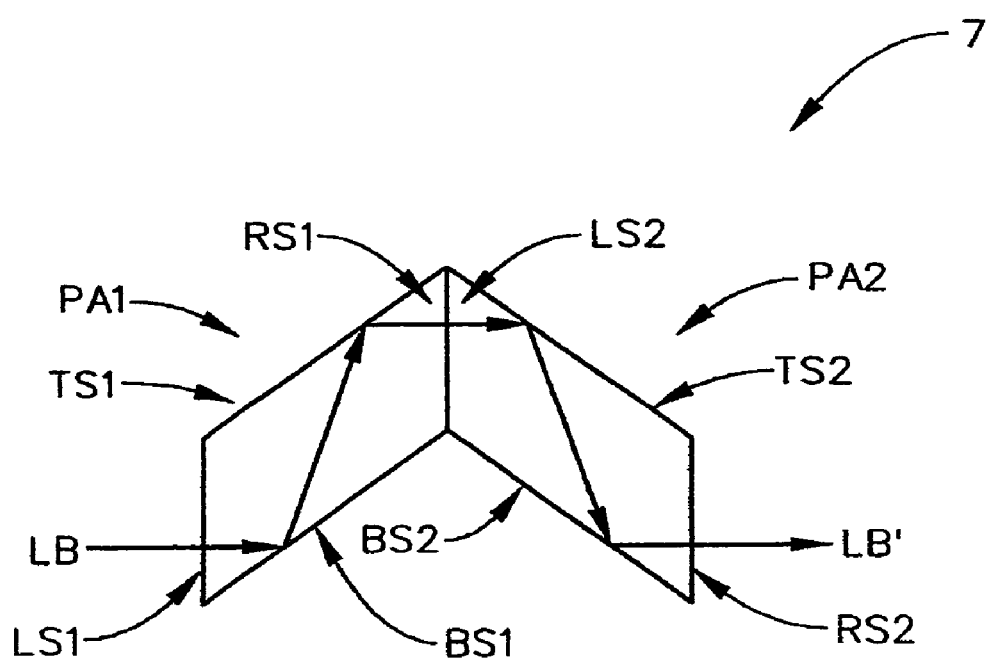

FIG. 3*p* shows that the fifth additional present invention retarder system (7) comprises first (PA1) and second (PA2) parallelogram shaped elements which, as viewed in side elevation, each have top (TS1)/(TS2) and bottom (BS1)/(BS2) sides parallel to one another, both said top (TS1) (TS2) and bottom (BS1) (BS2) sides each being oriented at an angle to horizontal. Said first (PA1) and second (PA2) parallelogram shaped elements also each have right (RS1)/(RS2) and left (LS1)/(LS2) sides parallel to one another, all said right (RS1) (RS2) and left (LS1) (LS2) sides being oriented essentially vertically. Said first (PA1) and second (PA2) parallelogram shaped elements are made of sample with an index of refraction greater than that of a surrounding ambient. A right most vertically oriented side (RS1) of said first parallelogram is in contact with a leftmost (LS2) vertically oriented side of the second parallelogram shaped element (PA2). In use an input beam of electromagnetic radiation (LB) caused to enter an essentially vertically oriented left side (LS1) of said first parallelogram shaped element (PA1) along an essentially horizontally oriented locus, is caused to be diffracted inside said retarder system and follow a locus which causes it to essentially totally internally reflect from internal interfaces of both said top (TS1) (TS2) and bottom (BS1) (BS2) sides of both said first and second parallelogram shaped elements (PA1) (PA2), then emerge from a right side (RS2) of said second parallelogram shaped element (PA2) along an essentially horizontally oriented locus as output beam of electromagnetic radiation (LB') which is undeviated and undisplaced from the essentially horizontally oriented locus of said input beam of essentially horizontally oriented electromagnetic radiation (LB). This is the case even when said retarder system (7) is caused to rotate. The result of said described retarder system (7) application being that retardation is entered between orthogonal components of said input electromagnetic beam of radiation (LB).

FIG. 3*n*1 shows that the sixth additional present invention retarder system (8) comprises first (BK1) and second (BK2) Berek-type retarders which each have an optical axes essentially perpendicular to a surface thereof. As shown by FIG. 3*n*2, each of said first (BK1) and second (BK2) Berek-type retarders can have fast axis which are oriented other than parallel to one another, but for the presently described retarder system it is assumed that the fast axes are aligned, (ie. an angle PHI ( ) of zero (0.0) degrees exists between fast axes of the two Berek-type (BK1) and (BK2) plates in FIG. 3*n*1. Said first and second Berek-type retarders each present with first and second essentially parallel sides. Said first (BK1) and second (BK2) Berek-type retarders are oriented, as viewed in side elevation, with first (LS1) and second (RS1) sides of one Berek-type retarder (BK1) being oriented other than parallel to first (LS2) and second (RS2) sides of the other Berek-type retarder (BK2). In use an incident beam of electromagnetic radiation (LB) is caused to impinge upon one of said first (BK1) Berek-type retarder on one side (LS1) thereof, partially transmit therethrough then impinge upon the second Berek-type retarder (BK2), on one side thereof (LS2), and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation. This is the case even when said retarder system (8) is caused to rotate. The result of said described retarder system (8) application being that retardation is entered between orthogonal components of said input electromagnetic beam of radiation. For insight it is mentioned that, in general, a Berek-type retarder is a uniaxial anisotropic plate with its optical axis essentially perpendicular to a surface thereof. The retardence introduced to an electromagnetic beam caused to transmit therethrough is determined by a tipping of said plate. The retardation system (8) having two such Berek-type retarders present, is, it is noted, insensitive to small angular deviations in an input electromagnetic beam as each plate contributes approximately hal of achieved retardence. This insensitivity results because if the input electromagnetic beam is slightly changed, one of said plates will contribute slightly more (less), but the second slightly less (more) retardence because of offsetting effective plate "tilts" with respect to electromagnetic beams input thereto. Also, said retarder system (8) is very nearly ideal in that the PSI component of the retarder system (8) is very near a constant forty-five (45) degrees. One problem however, is that Berek-type retarder plates exhibit a (1/wavelength) retardence characteristic which, without more, makes use over a wide spectral range difficult.

A variation of the just described retarder system (8) applies to the seventh additional present invention retarder system (9) as well, with the difference being that a FIG. 3*n*2 offset angle PHI (φ) other than zero (0.0) is present between fast axes of the two Berek-type plates. The description of the system remains otherwise unchanged. The benefit derived, however, is that a flatter than (1/wavelength) retardation characteristic can be achieved thereby.

FIG. 3o1 serves as the pictorial reference for the eighth additional present invention retarder system (10) which comprises first (BK1), second (BK2), third (BK3) and forth (BK4) Berek-type retarders which each have an optical axes essentially perpendicular to a surface thereof, each of which first (BK1) and second (BK2) Berek-type retarders has a fast axis, said fast axes in said first (BK1) and second (BK2) Berek-type retarders being oriented essentially parallel to one another. This is exemplified by FIG. 3o2. Said first (BK1) Berek-type retarder presents with first (LS1) and second (RS1) essentially parallel sides and said second (BK2) Berek-type retarders each present with first (LS2) and second (RS2) essentially parallel sides, and said first (BK1) and second (BK2) Berek-type retarders are oriented, as viewed in side elevation, with first (LS1) and second (RS1) sides of said first Berek-type retarder being oriented other than parallel to first (LS2) and second (RS2) sides of said second (BK2) Berek-type retarder. In use an incident beam of electromagnetic radiation (LB) is caused to impinge upon said first (BK1) Berek-type retarder on said first side (LS1) thereof, partially transmit therethrough then impinge upon the second (BK2) Berek-type retarder, on said first (LS2) side thereof, and partially transmit therethrough such that a polarized beam of electromagnetic radiation (LB') passing through both of said first (BK1) and second (BK2) Berek-type retarders emerges from the second thereof in a polarized state with a phase angle between orthogonal components therein which is different than that in the incident beam of electromagnetic radiation (LB), and in a direction which is an essentially undeviated and undisplaced from the incident beam of electromagnetic radiation (LB). Each of which third (BK3) and forth (BK4) Berek-type retarders also has a fast axis, and said fast axes in said third (BK3) and forth (BK4) Berek-type retarders are oriented essentially parallel to one another but other than parallel to the parallel fast axes of said first (BK1) and second (BK2) Berek-type retarders. Said third (BK3) Berek-type retarder presents with first (LS3) and second (RS3) essentially parallel sides, and said forth (BK4) Berek-type presents with first (LS4) and second (RS4) essentially parallel sides, and said first third (BK3) and forth (BK4) Berek-type retarders are oriented, as viewed in side elevation, with first (LS3) and second (RS3) sides of one of said third (BK3) Berek-type retarder being oriented other than parallel to first (LS4) and second (RS4) sides of said forth (BK4) Berek-type retarder; such that in use an incident beam of electromagnetic radiation (LB') exiting said second (BK2) Berek-type retarder is caused to impinge upon said third (BK3) Berek-type retarder on said first (LS3) side thereof, partially transmit therethrough then impinge upon said forth (BK4) Berek-type retarder on said first (LS4) side thereof, and partially transmit therethrough such that a polarized beam of electromagnetic radiation (LB') passing through said first (BK1), second (BK2), third (BK3) and forth (BK4) Berek-type retarders emerges from the forth (BK4) thereof in a polarized state with a phase angle between orthogonal components therein which is different than that in the incident beam of electromagnetic radiation (LB) caused to impinge upon the first (LS1) side of said first (BK1) Berek-type retarder, in a direction which is an essentially undeviated and undisplaced from said incident beam of electromagnetic radiation (LB). This is the case even when said retarder system (8) is caused to rotate. The result of said described retarder system (8) application being that retardation is entered between orthogonal components of said input electromagnetic beam of radiation.

A ninth additional present invention retarder system (11) is also pictorially represented by FIG. 3o1 and is similar to that just described excepting that the Berek-type retarder plates (BK1) and (BK2) fast axes need not be parallel to one another and the Berek-type retarder plates (BK3) and (BK4) need not be parallel to one another. However, if as a group Berek-type retarder plates ((BK1) and (BK2))/((BK3) and (BK4)) are parallel, they can be, but need not be parallel the fast axes of Berek-type retarder plates ((BK3) and (BK4))/((BK1) and (BK2)). This embodiment includes the case where all the fast axes of all Berek-type retarders (BK1), (BK2), (BK3) and (BK4) are all different.

Continuing, as described in the Disclosure of the invention Section of this Specification, as the polarizer in the present invention spectroscopic ellipsometer system remains fixed in position during data acquisition, it is preferable that a source of electromagnetic radiation, and/or a present Polarizer or Polarization State Generator be positioned or configured so as to pass predominately "S" Polarized electromagnetic radiation, as referenced to said beam combining system. The reason for this is that the split between transmission and reflection "S" polarization components is less, as a function of wavelength and electromagnetic beam angle-of-incidence to said beam combining means, compared to that between the "P" components.

It is noted that any of said source (LS) of polychromatic electromagnetic radiation can be Xenon or Duterium, and Quartz-Halogen lamps, or other suitable source.

It is also generally noted that the present invention spectroscopic ellipsometer system can, but not necessarily, utilize Zeiss Diode Array Spectrometer Systems identified by manufacturer numbers in the group: (MMS1 (300-1150 nm); UV/VIS MMS (190-730 nm); UV MMS (190-400 nm); and IR MMS (900-2400 nm)) as Detector System (DET). Said identified Zeiss systems provide a very compact system comprising a multiplicity of Detector Elements and provide focusing via a Focusing Element, Slit, and single concave holographic grating dispersive optics. However, any functional multi-element spectroscopic Detector arrangement is within the scope of the present invention.

FIGS. 4-6 are also included herein to provide insight to the Pseudo-Achromatic characteristics achieved by the FIG. 3f Compensator design. FIG. 4 shows a plot of such a compensator retardation characteristic which depends as (1/wavelength), (dashed line), as well as a present invention compensator characteristic, (solid line). The important thing to note is that a selected range of wavelengths over which a retardation of between seventy-five (75) and one-hundred-thirty (130) degrees is developed, is much greater for the present invention compensator. A present invention spectroscopic rotatable compensator ellipsometer system can comprise at least one compensator(s) which produces a retardance of, preferably, between seventy-five (75) and one-hundred-thirty (130) degrees over a range of wavelengths defined by a selection from the group consisting of:

a. between one-hundred-ninety (190) and seven-hundred-fifty (750) nanometers;

b. between two-hundred-forty-five (245) and nine-hundred (900) nanometers;

c. between three-hundred-eighty (380) and seventeen-hundred (1700) nanometers;

d. within a range of wavelengths defined by a maximum wavelength (MAXW) and a minimum wavelength (MINW) wherein the ratio of (MAXW)/(MINW) is at least one-and-eight-tenths (1.8).

Acceptable practice however, provides for the case wherein at least one of said at least one compensator(s) provides a retardation vs. wavelength characteristic retardation between thirty (30.0) and less than one-hundred-thirty-five (135) degrees over a range of wavelengths specified from MINW to MAXW by a selection from the group consisting of:
  a. MINW less than/equal to one-hundred-ninety (190) and MAXW greater than/equal to seventeen-hundred (1700);
  b. MINW less than/equal to two-hundred-twenty (220) and MAXW greater than/equal to one-thousand (1000) nanometers;
  c. within a range of wavelengths defined by a maximum wavelength (MAXW) and a minimum wavelength (MINW) range where (MAXW)/(MINW) is at least four-and one-half (4.5).

(NOTE, the specified vales and ranges can not be achieved by single plates with (1/wavelength) retardation characteristics).

More specifically, FIG. 5 shows calculated retardation vs. wavelength curves for two compensators which demonstrate (1/wavelength) retardation characteristics, (long and short dashed lines), and the retardation curve, (solid line), of a present invention assembly configuration as demonstrated in FIG. 3f which is arrived at by combining said two retarders with a 45 degree angle between the fast axes thereof. FIG. 6 shows a re-scaled plot of the solid line curve shown in FIG. 5.

Again, it is emphasised that the present application does not apply Compensators in a system which causes continuous rotation thereof during data acquisition, but can benefit from a Compensator designed to provide essentially constant Polarization State Modification effects over a Spectroscopic range of wavelengths.

Figure 7:
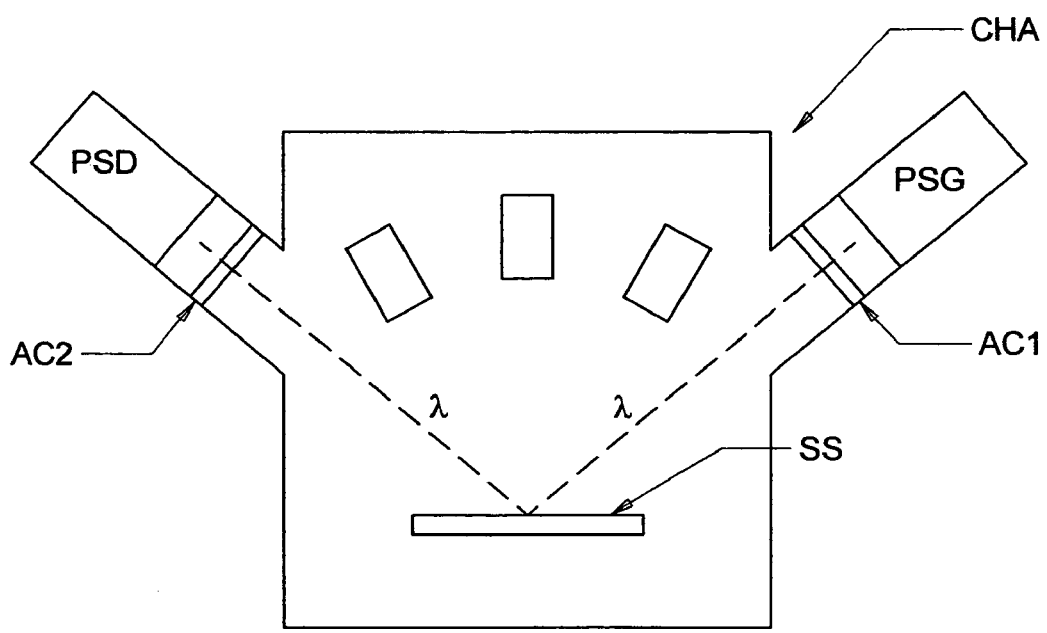
FIG. 7 shows the presently disclosed spectroscopic ellipsometer can be contained within a Chamber (CHA) System for controlling the ambient atmosphere.
Figure 10:
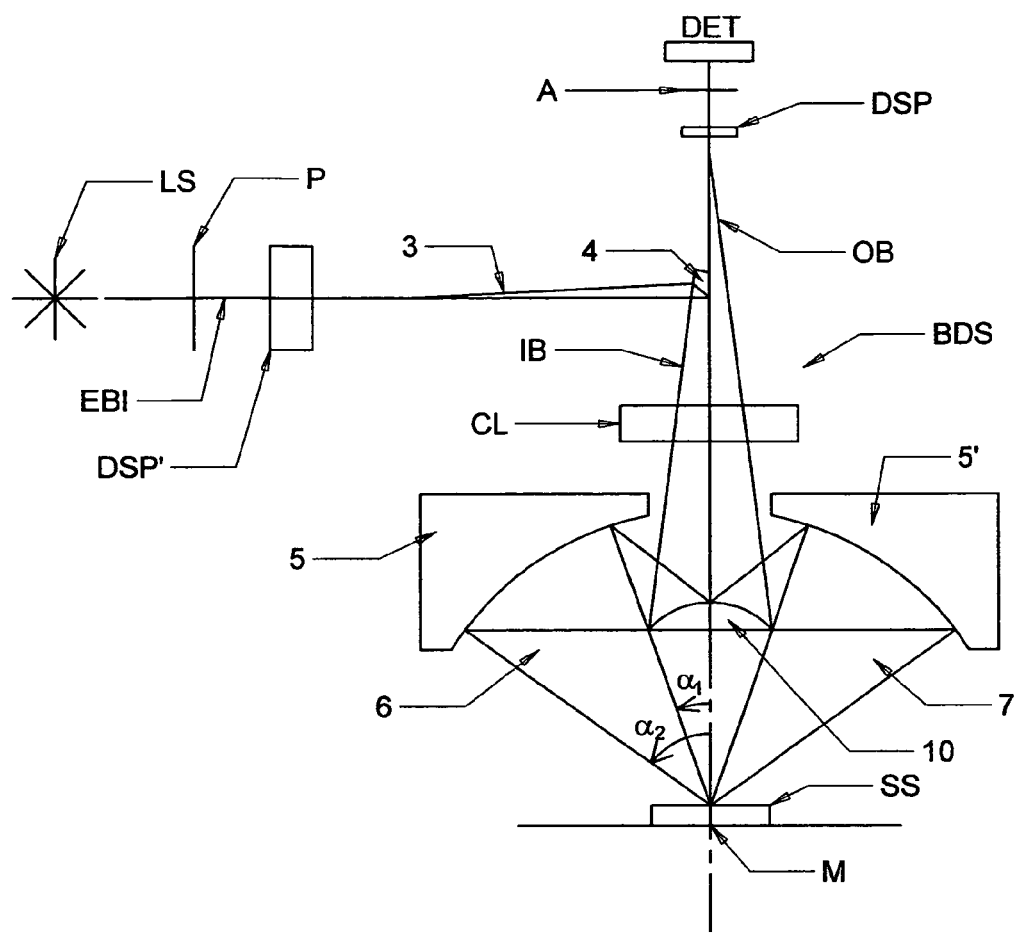
FIG. 10 shows the reflective optics of FIG. 8 combined with the components of a rotating or rotatable compensator ellipsometer.

FIG. 7 is included to disclose to show that the presently disclosed spectroscopic ellipsometer can be contained within a Chamber (CHA) System for controlling the ambient atmosphere. Possible Chamber configurations are:
  it comprises at least one chamber region in which is present polarization state generator (PSG) comprising component(s) prior to said sample system (SS), said sample system (SS), and polarization state detector (PSD) comprising component(s) after said sample system (SS);
  it comprises at least three chamber regions, in one of which is present polarization state generator (PSG) comprising component(s) prior to said sample system (SS), in the second of which is present the sample system (SS) and in the third of which is present polarization state detector (PSD) comprising component(s) after said sample system (SS);
  it comprises at least two chamber regions, in one of which is present polarization state generator (PSG) comprising component(s) prior to said sample system (SS) and said sample system (SS), and in the second of which is present polarization state detector (PSD) comprising component(s) after said sample system (SS);
  it comprises at least two chamber regions, in one of which is present polarization state generator (PSD) comprising component(s) prior to said sample system (SS), and in the second of which is present polarization state detector (PSD) comprising component(s) after said sample system (SS) and said sample system (SS);

where the combination of elements (LS), (P), and (CMP') in FIG. 1 is described as a Polarization State Generation System (PSG), and the combination of elements (CMP) (A) and (DET) is described as a Polarization State Detection System (PSD).

Figure 8:
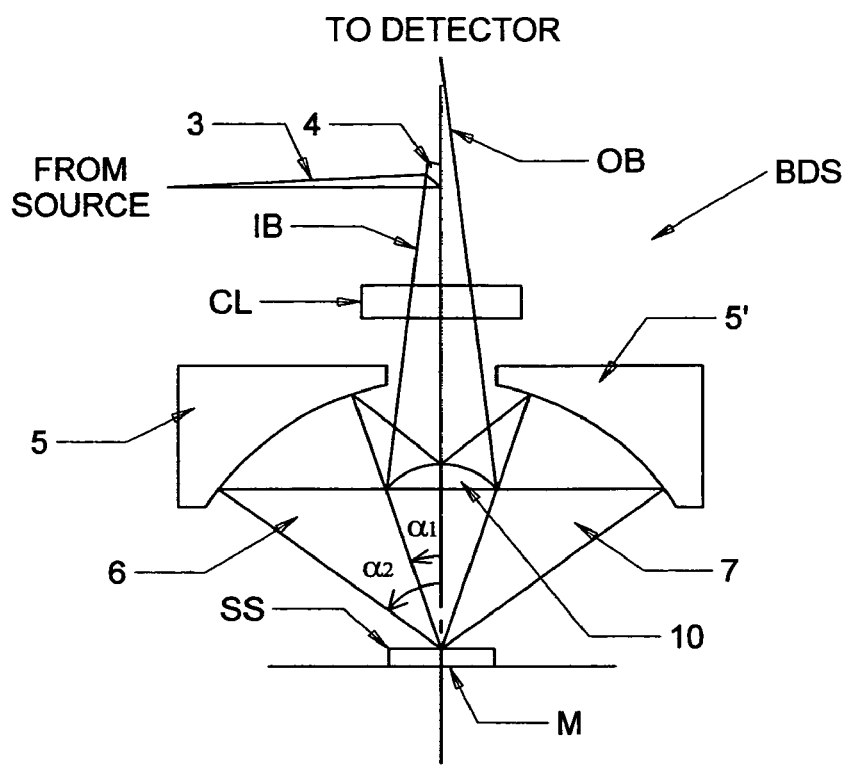
FIG. 8 shows the system of the disclosed invention reflective optics.

Continuing, FIG. 8 shows that the disclosed invention Beam Directing system comprises:
  substantially Planar Mirror (4);
  Convex Spherical Mirror (10);
  Concave Spherical Mirror (5);
  Concave Spherical Mirror (5');
  Aberation Correction System (CL) means.

In use substantially Planar Mirror (4) directs a beam of electromagnetic radiation (3) to reflect therefrom and proceed as Beam (IB) to reflect from Convex Spherical Mirror (10), to Concave Spherical Mirror (5) which focuses it, as Incident Beam (6) to a spot (M) on Sample (SS), reflected electromagnetic radiation (7) from said Spot (M) on said Sample (SS) being collected by Concave Spherical Mirror (51), which reflectively directs it to reflect from Convex Spherical Mirror (10) and emerge as Output Beam (OB).

Further, a beam of electromagnetic radiation (IB) reflects from a substantially Planar Mirror (4), then proceeds to reflect from Convex Spherical Mirror (10), to Concave Spherical Mirror (5) which focuses it, as Incident Beam to a spot (M) on Sample (SS) at an angle-of-incidence. Reflected electromagnetic radiation from said Spot (M) on said Sample (SS) is collected by Concave Spherical Mirror (5'), which directs it to reflect from Convex Spherical Mirror (10) and emerge as Beam (OB). Note in particular that an Aberation Correction System (CL) is present, and that both Input (IB) and Output Beams (OB) pass therethrough.

Said input (IB) and output (OB) Aberation Correction System (CL) means is positioned so that both Input (IB) and output (OB) Beams pass therethrough so that electromagnetic radiation reflected from each of the spherical mirrors (5) and (5') is corrected thereby for spherical aberation. This configuration for using the same refractive element (CL) to correct both incident and reflected electromagnetic radiation is believed unique over the prior art.

It is to be appreciated that the Spherical Mirrors (5) and (5') can be separate Mirrors and FIG. 1 does not necessarily imply a cross-sectional through a 360 Degree Donut/Torroidal Shaped Mirror.

Importantly, the substantially Planar Mirror (4) is mounted on a slider or functional equivalent to enable its sequential positioning as demonstrated in FIG. 11.

Figure 9A:
FIGS. 9a, 9b and 9c show demonstrative lens configurations.
Figure 9B:
Figure 9C:
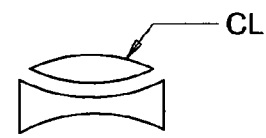

FIGS. 9a, 9b and 9c show possible configurations of lens elements. The FIG. 9a configuration can comprise elements made of Fused Silica and CaF2. While a FIG. 9b configuration would probably not be achromatic, it might perform an acceptable function. Preferred Lens Configurations, as shown in FIGS. 9a and 9c comprise multiple elements which can provide substantially achromatic characteristics. Also, it is preferred that the Lens System (CL) be of about Zero Power. Said Aberation Correction System (CL) means can comprise a combination of two miniscus lenses, or be a bi-convex lens, or be of any functional refractive design.

Said input (IB) and output (OB) Aberation Correction System (CL) means is positioned so that both Input (IB) and Output (OB) Beams pass therethrough.

A benefit of the shown focusing configuration is that it produces approximately circular spots on a sample (SS), rather than an elongated spot typical when beam of electromagnetic radiation are directed onto a sample at an oblique angle.

No known system provides at least one Concave Spherical Mirror (5) and (5') functionally positioned with the Convex Spherical Mirror (10) as shown in a FIG. 8. Note that additional Concave Spherical Mirrors could also be present and located as would result if (5) and (5') were rotated 90 Degrees about a vertically oriented line.

Turning now to FIG. 11 there is shown an enlarged partial view of the system shown in FIG. 8. Note that the substantially Planar Mirror (4) is shown in a plurality of horizontally located positions and the effect said positioning has on the angle-of-incidence at which the beam eventually arrives at the Sample (SS). The effect is achieved by providing a substantially Planar Mirror (4) which has a relatively small reflective surface, as opposed to a reflective surface of a size to simultaneously provide reflected electromagentic radiation over a large portion of Convex Spherical Mirror (10). Prior art systems have used a large reflective area substantially Planar Mirror (4). A working definition of a small reflecting area substantially Planar Mirror (4) is that the nominal angle-of-incidence effected at a sample (SS) by a beam reflecting therefrom will comprise a standard deviation of not mor that +/−2 degrees about the mean, although a larger standard deviation could still enable obtaining useful results. Importantly, the substantially Planar Mirror (4) is then mounted on a slider, or functional equivalent, to enable its sequential, angle-of-incidence changing positioning, as demonstrated in FIG. 11.

FIG. 12 is included to show that a plurality of duplicate systems can be oriented so as to direct beams of electromagnetic radiation (3) (3') produced thereby toward the Convex Spherical Mirror (10) thereof. Note that the angle at which the beam of electromagnetic radiation (3) approaches said Convex Spherical Mirror (16) is offset by a demonstrative 90 degrees from the beam of electromagnetic radiation (3') produced by a second said duplicate systems, where said offset angle is viewed as a rotation angle from above said Convex Spherical Mirror (10). Note also that the location of substantially Planar Mirrors (4) and (4') are not the same, as measured with, for instance, respect to the center of the Convex Spherical Mirror (10). As demonstrated in FIG. 11, different such positioning of substantially Planar Mirrors (4) and (4') allows simultaneous application of beams of electromagnetic radiation at more than one angle-of-incidence to sample (SS). Further, separate monitoring of each beam after it emerges from the system as a beam (OB) of said system, via reflection from the Convex Spherical Mirror (10), is easily achieved. It is also mentioned that as Convex Spherical Mirror (10) is a single rotated element, FIG. 12 is demonstrative. There could be more than two systems present, say three or four rotated at 60 or 45 degrees, respectively, to one another, or at any other angles with respect to one another.

It is noted that other terminology Polarizer (P), Analyzer (A), Compensator (C) include any element which performs the described function.

It is to be understood that the terminology "spectroscopic ellipsometer system is to be read with sufficient breadth to include spectroscopic polarimeter and the like systems.

Finally, as regards the Concave Spherical Mirrors (5) and (5'), where Patentability is supported by the angle-of-incidence controlling movability of substantially Planar Mirror (4), said Concave Spherical Mirrors (5) and (5') can be separate mirrors or regions of a torroidal mirror which is rotated about an axis co-linear with that about which Convex Spherical Mirror (10) is rotated. Where necessary to support-Patentability, said Concave Spherical Mirrors (5) and (5') should be considered as separate elements.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for monitoring change in:
   the intensity of; and/or
   the ratio of and/or the phase between orthogonal components in;
a spectroscopic beam of electromagnetic radiation, which is caused by interaction with a sample system (SS);
said system comprising:
   a source of electromagnetic radiation (LS);
   a beam directing system (BDS) comprising:
      a substantially planar mirror (4);
      a convex spherical mirror (10);
      at least one concave spherical mirror (5) (5'); and
      aberation correction system (CL) means;
   such that in use substantially planar mirror (4) directs an input beam (IB) of electromagnetic radiation (3) to reflect therefrom and proceed to reflect from said convex spherical mirror (10), and from said at least one concave spherical mirror (5) which focuses it, as incident beam (6) to a spot (M) on sample (SS), reflected electromagnetic radiation (7) from said spot (M) on said sample (SS) being collected by said at least one concave spherical mirror (5'), which reflectively directs it to reflect from convex spherical mirror (10) and emerge as an output beam (OB);
   said aberation correction system (CL) means being positioned so that both input (IB) and output (OB) beams pass therethrough; and
   a detector (DET) of electromagnetic radiation;
   said system further comprising at least one rotating or rotatable compensator (CMP) (CMP') positioned so that said beam of electromagnetic radiation transmits therethrough;
such that in use, said source (LS) of electromagnetic radiation provides an input beam (EBI) of electromagnetic radiation to said beam directing system (BDS), which in turn causes said input beam (EBI) of electromagnetic radiation to interact with said spot (M) on said sample (SS) and then proceed as output beam (EBO) into said detector (DET) of electromagnetic radiation, as said at least one rotating or rotable compensator (CMP) (CMP') is caused to continuously rotate or step through sequence of descrete positions.

2. A system as in claim 1 which further comprises a polarizer (P) between said source (LS) of electromagnetic radiation and said beam directing system (BDS), and an analyzer (A) between said beam directing system (BDS) and said detector (DET) of electromagnetic radiation and said system is an ellipsometer, polarimeter or the like system.

3. A system as in claim 1, in which said substantially planar mirror (4) is movable so as to enable its directing said beam of electromagnetic radiation (3) toward said convex spherical mirror (10) at different locations thereon, such that said beam of electromagnetic radiation (3) approaches said sample (SS) at determinable angles-of-incidence.

4. A system as in claim 1, in which the aberation correction system (CL) means is achromatic and is further optionally characterized by a selection from the group consisting of:
   aberation correction system (CL) means is appoximately zero power;
   aberation correction system (CL) means is a combination of two miniscus lenses; and aberation correction system (CL) means is a bi-convex lens.

5. A system as in claim 1 wherein said at least one compensator (CMP) is characterized by a selection from the group consisting of:
   said at least one compensator produces a retardance of between seventy-five (75) and one-hundred-thirty (130) degrees over a range of wavelengths defined by a selection from the group consisting of:
   a. between one-hundred-ninety (190) and seven-hundred-fifty (750) nanometers;
   b. between two-hundred-forty-five (245) and nine-hundred (900) nanometers;
   c. between three-hundred-eighty (380) and seventeen-hundred (1700) nanometers;
   d. within a range of wavelengths defined by a maximum wavelength (MAXW) and a minimum wavelength (MINW) wherein the ratio of (MAXW)/(MINW) is at least one-and-eight-tenths (1.8); and
   said at least one compensator produces a retardation between thirty (30.0) and less than one-hundred-thirty-five (135) degrees over a range of wavelengths specified from MINW to MAXW by a selection from the group consisting of:
   a. MINW less than or equal to one-hundred-ninety (190) and MAXW greater than or equal to seventeen-hundred (1700);
   b. MINW less than or equal to two-hundred-twenty (220) and MAXW greater than/equal to one-thousand (1000) nanometers;
   c. within a range of wavelengths defined by a maximum wavelength (MAXW) and a minimum wavelength (MINW) range where
   (MAXW)/(MINW) is at least four-and one-half (4.5).

6. A system as in claim 1 comprising at least one additional complete duplicate of said beam directing (BDS) system comprising:
   substantially planar mirror (4);
   convex spherical mirror (10);
   at least one concave spherical mirror (5) (5'); and
   aberation correction system (CL) means;
   such that in use substantially planar mirror (4) directs a beam of electromagnetic radiation (3) to reflect therefrom and proceed as beam (IB) to reflect from convex spherical mirror (10), and from concave spherical mirror (5) which focuses it, as incident beam (6) to a spot (M) on sample (SS), reflected electromagnetic radiation (7) from said spot (M) on said sample (SS) being collected by concave spherical mirror (5'), which reflectively directs it to reflect from convex spherical mirror (10) and emerge as an output beam (OB);
   said aberation correction system (CL) means being positioned so that both input (IB) and output (OB) beams pass therethrough;
   each said duplicate system being oriented so as to direct a beam of electromagnetic radiation (3) produced thereby toward the convex spherical mirror (10) thereof at an angle offset from the beam of electromagnetic radiation (3) produced by other of said duplicate systems, said offset angle being viewed as a rotation angle from above said convex spherical mirror (10).

7. A system as in claim 6, in which the aberation correction system (CL) means in each of said at least one duplicate system is achromatic and of approximately zero power.

8. A system as in claim 7, in which the aberation correction system (CL) means in each of said at least one duplicate system is a bi-convex lens.

9. A system as in claim 6, in which the aberation correction system (CL) means in each of said at least one duplicate system is a combination of two miniscus lenses.

10. A system as in claim 1 in which, during data collection by said detector, said at least one compensator is caused to perform motion selected from the group consisting of:
    continuously rotates; and
    sequentially rotates through a plurality of discrete angles;
    around an axis defined by the locus of the spectroscopic electromagnetic beam as it transmits therethrough.

11. A system as in claim 1 which is present in a chamber configured as a selection from the group consisting of:
    it comprises at least one chamber region in which is present polarization state generator comprising component(s) prior to said sample system, said sample system, and polarization state detector comprising component(s) after said sample system;
    it comprises at least three chamber regions, in one of which is present polarization state generator comprising component(s) prior to said sample system, in the second of which is present the sample system and in the third of which is present polarization state detector comprising component(s) after said sample system;
    it comprises at least two chamber regions, in one of which is present polarization state generator comprising component(s) prior to said sample system and said sample system, and in the second of which is present polarization state detector comprising component(s) after said sample system;
    it comprises at least two chamber regions, in one of which is present polarization state generator comprising component(s) prior to said sample system, and in the second of which is present polarization state detector comprising component(s) after said sample system and said sample system.

12. A method of monitoring the effect a sample has on a beam of electromagnetic radiation by interaction therewith, comprising the steps of:
    a) providing a system for monitoring change in:
       the intensity of; and/or
       the ratio of and/or the phase between orthogonal components in;
    a spectroscopic beam of electromagnetic radiation which is caused by interaction with a sample system;
    said system comprising:
       a source of electromagnetic radiation;
       a beam directing system comprising:
          a substantially planar mirror;
          a convex spherical mirror;
          at least one concave spherical mirror; and
          aberation correction system means;
       such that in use said substantially planar mirror directs an input beam of electromagnetic radiation to reflect therefrom and proceed to reflect from said convex spherical mirror, and from said at least one concave spherical mirror which focuses it, as incident beam to a spot on sample, reflected electromagnetic radiation from said spot on said sample being collected by said at least one concave spherical mirror, which reflectively directs it to reflect from said convex spherical mirror and emerge as an output beam;
       said aberation correction system means optionally being positioned so that both input and output beams pass therethrough; and
       a detector of electromagnetic radiation;

said system further comprising at least one rotating or rotatable compensator positioned so that said beam of electromagnetic radiation transmits therethrough;

such that in use said source of electromagnetic radiation provides an input beam of electromagnetic radiation to said beam directing system, which in turn causes said input beam of electromagnetic radiation to interact with said spot on said sample and then proceed as an output beam into said detector of electromagnetic radiation, as said rotating or rotable compensator is caused to continuously rotate or step through sequence of descrete positions;

b) causing said source of electromagnetic radiation to produce an input beam thereof and direct it toward said beam directing system;

c) causing said detector of electromagentic radiation to monitor said input beam of electromagnetic radiation after it emerges from said beam directing system as said output beam and comparing the:
the intensity thereof; and/or
the ratio of and/or the phase between orthogonal components therein, to the same attributes of the input beam directly provided by the source of said beam of electromagnetic radiation.

13. A spectroscopic ellipsometer system comprising:
a source of polychromatic electromagnetic radiation;
a polarizer which remains fixed in position during data acquisition;
a stage for supporting a sample system;
an analyzer which remains fixed in position during data acquisition; and
a multi-element spectroscopic detector system;
said spectroscopic ellipsometer system further comprising at least one rotating or rotatable compensator for sequentially modifying a polarization state of a beam of electromagnetic radiation provided by said source of polychromatic electromagnetic radiation through a plurality of polarization states, said rotating or rotatable compensator means for sequentially modifying a polarization state of a beam of electromagnetic radiation provided by said source of polychromatic electromagnetic radiation through a plurality of polarization states being present at least one location selected from the group consisting of:
between said polarizer and said stage for supporting a sample system; and
between said stage for supporting a sample system and said analyzer;
and positioned so that said beam of electromagnetic radiation transmits therethrough in use;
said spectroscopic ellipsometer system further comprising, between said polarizer and analyzer, a beam directing system for causeing an input beam of electromagentic radiation to impinge on spot on a sample system, said beam directing system comprising:
a substantially planar mirror;
a convex spherical mirror;
at least one concave spherical mirror; and
aberation correction system means;
such that in use said substantially planar mirror directs an input beam of electromagnetic radiation to reflect therefrom and proceed as a beam to reflect from said convex spherical mirror, and from said at least one concave spherical mirror which focuses it, as incident beam to a spot on sample, reflected electromagnetic radiation from said spot on said sample being collected by said at least one concave spherical mirror, which reflectively directs it to reflect from said convex spherical mirror and emerge as an output beam;

said aberation correction system means optionally being positioned so that both input and output beams pass therethrough;

said at least one compensator means comprising at least one rotatable compensator selected from the group consisting of:

a) a selection from the group consisting of:
a single element compensator; and
a multiple element compensator;

b) a compensator comprised of at least two per se. zero-order waveplates (MOA) and (MOB), said per se. zero-order waveplates (MOA) and (MOB) having their respective fast axes rotated to a position offset from zero or ninety degrees with respect to one another, with a nominal value being forty-five degrees;

c) a compensator comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position at a nominal forty-five degrees to the fast axes (FAA1) and (FAB1), respectively, of the multiple order waveplates (MOA1) and (MOB1) in said first effective zero-order waveplate (ZO1);

d) a compensator comprised of a combination of at least a first (ZO1) and a second (ZO2) effective zero-order wave plate, said first (ZO1) effective zero-order wave plate being comprised of two multiple order waveplates (MOA1) and (MOB1) which are combined with the fast axes thereof oriented at a nominal ninety degrees to one another, and said second (ZO2) effective zero-order wave plate being comprised of two multiple order waveplates (MOA2) and (MOB2) which are combined with the fast axes thereof oriented at a nominal ninety degrees to one another; the fast axes (FAA2) and (FAB2) of the multiple order waveplates (MOA2) and (MOB2) in said second effective zero-order wave plate (ZO2) being rotated to a position away from zero or ninety degrees with respect to the fast axes (FAA1) and (FAB1), respectively, of the multiple order waveplates (MOA1) and (MOB1) in said first effective zero-order waveplate (ZO1);

e) a compensator comprised of at least one zero-order waveplate, ((MOA) or (MOB)), and at least one effective zero-order waveplate, ((ZO2) or (ZO1) respectively), said effective zero-order wave plate, ((ZO2) or (ZO1)), being comprised of two multiple order waveplates which are combined with the fast axes thereof oriented at a nominal ninety degrees to one another, the fast axes of the multiple order waveplates in said effective zero-order wave plate, ((ZO2) or (ZO1)), being rotated to a position away from zero or ninety degrees with respect to the fast axis of the zero-order waveplate, ((MOA) or (MOB));

f) a compensator system comprised of a first triangular shaped element, which as viewed in side elevation presents with first and second sides which project to the left and right and downward from an upper point, which first triangular shaped element first and second sides have reflective outer surfaces; said retarder system further comprising a second triangular shaped element which as viewed in side elevation presents with first and second sides which project to the left and right and downward from an upper point, said second triangular shaped element being made of sample which provides reflective interfaces on first and second sides inside thereof; said second triangular shaped element being oriented with respect to the first triangular shaped element such that the upper point of said second triangular shaped element is oriented essentially vertically directly above the upper point of said first triangular shaped element; such that in use an input electromagnetic beam of radiation caused to approach one of said first and second sides of said first triangular shaped element along an essentially horizontally oriented locus, is caused to externally reflect from an outer surface thereof and travel along a locus which is essentially upwardly vertically oriented, then enter said second triangular shaped element and essentially totally internally reflect from one of said first and second sides thereof, then proceed along an essentially horizontal locus and essentially totally internally reflect from the other of said first and second sides and proceed along an essentially downward vertically oriented locus, then externally reflect from the other of said first and second sides of said first triangular shaped elements and proceed along an essentially horizontally oriented locus which is undeviated and undisplaced from the essentially horizontally oriented locus of said input beam of essentially horizontally oriented electromagnetic radiation; with a result being that retardation is entered between orthogonal components of said input electromagnetic beam of radiation;

g) a compensator system comprised of, as viewed in upright side elevation, first and second orientation adjustable mirrored elements which each have reflective surfaces; said compensator system further comprising a third element which, as viewed in upright side elevation, presents with first and second sides which project to the left and right and downward from an upper point, said third element being made of sample which provides reflective interfaces on first and second sides inside thereof; said third element being oriented with respect to said first and second orientation adjustable mirrored elements such that in use an input electromagnetic beam of radiation caused to approach one of said first and second orientation adjustable mirrored elements along an essentially horizontally oriented locus, is caused to externally reflect therefrom and travel along a locus which is essentially upwardly vertically oriented, then enter said third element and essentially totally internally reflect from one of said first and second sides thereof, then proceed along an essentially horizontal locus and essentially totally internally reflect from the other of said first and second sides and proceed along an essentially downward vertically oriented locus, then reflect from the other of said first and second orientation adjustable mirrored elements and proceed along an essentially horizontally oriented propagation direction locus which is essentially undeviated and undisplaced from the essentially horizontally oriented propagation direction locus of said input beam of essentially horizontally oriented electromagnetic radiation; with a result being that retardation is entered between orthogonal components of said input electromagnetic beam of radiation;

h) a compensator system comprised of a parallelogram shaped element which, as viewed in side elevation, has top and bottom sides parallel to one another, both said top and bottom sides being oriented essentially horizontally, said retarder system also having right and left sides parallel to one another, both said right and left sides being oriented at an angle to horizontal, said retarder being made of a sample with an index of refraction greater than that of a surrounding ambient; such that in use an input beam of electromagnetic radiation caused to enter a side of said retarder selected from the group consisting of:
right and left;
along an essentially horizontally oriented locus, is caused to diffracted inside said retarder system and follow a locus which causes it to essentially totally internally reflect from internal interfaces of both said top and bottom sides, and emerge from said retarder system from a side selected from the group consisting of:
left and right respectively;
along an essentially horizontally oriented locus which is undeviated and undisplaced from the essentially horizontally oriented locus of said input beam of essentially horizontally oriented electromagnetic radiation; with a result being that retardation is entered between orthogonal components of said input electromagnetic beam of radiation;

i) a compensator system comprised of first and second triangular shaped elements, said first triangular shaped element, as viewed in side elevation, presenting with first and second sides which project to the left and right and downward from an upper point, said first triangular shaped element further comprising a third side which is oriented essentially horizontally and which is continuous with, and present below said first and second sides; and said second triangular shaped element, as viewed in side elevation, presenting with first and second sides which project to the left and right and upward from an upper point, said second triangular shaped element further comprising a third side which is oriented essentially horizontally and which is continuous with, and present above said first and second sides; said first and second triangular shaped elements being positioned so that a rightmost side of one of said first and second triangular shaped elements is in contact with a leftmost side of the other of said first and second triangular shaped elements over at least a portion of the lengths thereof; said first and second triangular shaped elements each being made of sample with an index of refraction greater than that of a surrounding ambient; such that in use an input beam of electromagnetic radiation caused to enter a side of a triangular shaped element selected from the group consisting of:
first and second;
not in contact with said other triangular shape element, is caused to diffracted inside said retarder and follow a locus which causes it to essentially totally internally reflect from internal interfaces of said third sides of each of said first and second triangular shaped elements, and emerge from a side of said triangular shaped element selected from the group consisting of:
second and first;
not in contact with said other triangular shape element, along an essentially horizontally oriented locus which is undeviated and undisplaced from the essentially horizontally oriented locus of said input beam of essentially horizontally oriented electromagnetic radiation;

with a result being that retardation is entered between orthogonal components of said input electromagnetic beam of radiation;

j) a compensator system comprised of a triangular shaped element, which as viewed in side elevation presents with first and second sides which project to the left and right and downward from an upper point, said retarder system further comprising a third side which is oriented essentially horizontally and which is continuous with, and present below said first and second sides; said retarder system being made of a sample with an index of refraction greater than that of a surrounding ambient; such that in use a an input beam of electromagnetic radiation caused to enter a side of said retarder system selected from the group consisting of:
first and second;
along an essentially horizontally oriented locus, is caused to diffracted inside said retarder system and follow a locus which causes it to essentially totally internally reflect from internal interface of said third sides, and emerge from said retarder from a side selected from the group consisting of:
second and first respectively;
along an essentially horizontally oriented locus which is undeviated and undisplaced from the essentially horizontally oriented locus of said input beam of essentially horizontally oriented electromagnetic radiation; with a result being that retardation is entered between orthogonal components of said input electromagnetic beam of radiation;

k) a compensator system comprised of first and second Berek-type retarders which each have an optical axes essentially perpendicular to a surface thereof, each of which first and second Berek-type retarders has a fast axis, said fast axes in said first and second Berek-type retarders being oriented in an orientation selected from the group consisting of:
parallel to one another; and
other than parallel to one another;
said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation; with a result being that retardation is entered between orthogonal components of said input electromagnetic beam of radiation;

l) a compensator system comprised of first and second Berek-type retarders which each have an optical axes essentially perpendicular to a surface thereof, each of which first and second Berek-type retarders has a fast axis, said fast axes in said first and second Berek-type retarders being oriented other than parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation, said compensator system further comprising third and forth Berek-type retarders which each have an optical axes essentially perpendicular to a surface thereof, each of which third and forth Berek-type retarders has a fast axis, said fast axes in said third and forth Berek-type retarders being oriented other than parallel to one another, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation; with a result being that retardation is entered between orthogonal components of said input electromagnetic beam of radiation;

m) a compensator system comprised of first, second, third and forth Berek-type retarders which each have an optical axes essentially perpendicular to a surface thereof, each of which first and second Berek-type retarders has a fast axis, said fast axes in said first and second Berek-type retarders being oriented essentially parallel to one another; said first and second Berek-type retarders each presenting with first and second essentially parallel sides, and said first and second Berek-type retarders being oriented, as viewed in side elevation, with first and second sides of one Berek-type retarder being oriented other than parallel to first and second sides of the other Berek-type retarder; such that in use an incident beam of electromagnetic radiation is caused to impinge upon one of said first and second Berek-type retarders on one side thereof, partially transmit therethrough then impinge upon the second Berek-type retarder, on one side thereof, and partially transmit therethrough such that a polarized beam of electromagnetic radiation passing through both of said first and second Berek-type retarders emerges from the second thereof in a polarized state with a phase angle between orthogonal components therein which is different than that in the incident beam of electromagnetic radiation, and in a propagation direction which is essentially undeviated and undisplaced from the incident beam of electromagnetic radiation; each of which third and forth Berek-type retarders has a fast axis, said fast axes in said third and forth Berek-type retarders being oriented essentially parallel to one another but other than parallel to the fast axes of said first and second Berek-type retarders, said third and forth Berek-type retarders each presenting with first and second essentially parallel sides, and said third and forth Berek-type retarders being oriented, as viewed in side elevation, with first and second sides of one of said third and forth Berek-type retarders being oriented other than parallel to first and second sides of said forth Berek-type retarder; such that in use an incident beam of electromagnetic radiation exiting said second Berek-type retarder is caused to impinge upon said third Berek-type retarder on one side thereof, partially transmit therethrough then impinge upon said forth Berek-type retarder on one side thereof, and partially transmit therethrough such that a polarized beam of electromagnetic radiation passing through said first, second, third and forth Berek-type retarders emerges from the forth thereof in a polarized state with a phase angle between orthogonal components therein which is different than that in the incident beam of electromagnetic radiation caused to impinge upon the first side of said first Berek-type retarder, and in a direction which is essentially undeviated and undisplaced from said incident beam of electromagnetic radiation; with a result being that retardation is entered between orthogonal components of said input electromagnetic beam of radiation; said compensator causing essentially no deviation or displacement in a polychromatic beam of electromagnetic radiation caused to pass therethrough while caused to rotate.

14. A system as in claim 13 which is present in a chamber configured as a selection from the group consisting of:
  it comprises at least one chamber region in which is present polarization state generator comprising component(s) prior to said sample system, said sample system, and polarization state detector comprising component(s) after said sample system;
  it comprises at least three chamber regions, in one of which is present polarization state generator comprising component(s) prior to said sample system, in the second of which is present the sample system and in the third of which is present polarization state detector comprising component(s) after said sample system;
  it comprises at least two chamber regions, in one of which is present polarization state generator comprising component(s) prior to said sample system and said sample system, and in the second of which is present polarization state detector comprising component(s) after said sample system;
  it comprises at least two chamber regions, in one of which is present polarization state generator comprising component(s) prior to said sample system, and in the second of which is present polarization state detector comprising component(s) after said sample system and said sample system.

15. A spectroscopic ellipsometer sequentially comprising:
  a) a source of a spectroscopic beam electromagnetic radiation;
  b) a polarizer element;
in either order elements c and d:
  c) a rotating or rotatable compensator element;
  d) a reflective optic input system;
  e) a sample system;
in either order elements f and q:
  f) a reflective optic output system;
  g) a rotating or rotatable compensator element;
  h) an analyzer element; and
  i) a spectroscopic detector system;
at least one of said rotating or rotatable compensator elements in c or q being present and oriented so that a spectroscopic electromagnetic beam provided by the source thereof transmits therethrough along its axis of rotation;
in which said reflective optic input system, sample system, and said reflective optic output system comprise a beam directing system comprising:
  a substantially planar mirror;
  a convex spherical mirror;
  at least one concave spherical mirror; and
  aberation correction system means;
such that in use said substantially planar mirror directs an input beam of electromagnetic radiation to reflect therefrom and proceed to reflect from said convex spherical mirror, and from said at least one concave spherical mirror which focuses it, as incident beam to a spot on sample, reflected electromagnetic radiation from said spot on said sample being collected by said at least one concave spherical mirror, which reflectively directs it to reflect from said convex spherical mirror and emerge as an output beam;
  said aberation correction system means being positioned so that both input and output beams pass therethrough;
such that in use, said source of electromagnetic radiation provides said input beam of electromagnetic radiation to said beam directing system, which in turn causes said input beam of electromagnetic radiation to interact with said spot on said sample and then proceed as said output beam into said detector of electromagnetic radiation, as said rotating or rotable compensator is caused to continuously rotate or step through sequence of descrete positions.

16. A spectroscopic ellipsometer system comprising a source of a polychromatic beam of electromagnetic radiation, a polarizer, a stage for supporting a sample system, an analyzer, a dispersive optics and at least one detector system which comprises a multiplicity of detector elements, said spectroscopic ellipsometer system further comprising at least one compensator(s) positioned at a location selected from the group consisting of:
  before said stage for supporting a sample system;
  after said stage for supporting a sample system; and
  both before and after said stage for supporting a sample system;
such that when said spectroscopic ellipsometer system is used to investigate a sample system present on said stage for supporting a sample system at least one of said at least one compensator(s) is caused to continuously rotate while a polychromatic beam of electromagnetic radiation produced by said source of a polychromatic beam of electromagnetic radiation is caused to pass through said polarizer and said at least one compensator(s), said polychromatic beam of electromagnetic radiation being also caused to interact with a sample system on said stage for supporting a sample system, pass through said analyzer and interact with said dispersive optics such that a multiplicity of essentially single wavelengths are caused to simultaneously enter a corresponding multiplicity of detector elements in said at least one detector system;

said spectroscopic ellipsometer system being characterized by:

a beam directing system comprising:
    a substantially planar mirror;
    a convex spherical mirror;
    at least one concave spherical mirror; and
    aberation correction system means;
    such that in use said substantially planar mirror directs an input beam of electromagnetic radiation to reflect therefrom and proceed to reflect from said convex spherical mirror, and from said at least one concave spherical mirror which focuses it, as incident beam to a spot on sample, reflected electromagnetic radiation from said spot on said sample being collected by said at least one concave spherical mirror, which reflectively directs it to reflect from said convex spherical mirror and emerge as an output beam;
    said aberation correction system means being positioned so that both input and output beams pass therethrough.

17. A system as in claim 16 which is present in a chamber configured as a selection from the group consisting of:

it comprises at least one chamber region in which is present polarization state generator comprising component(s) prior to said sample system, said sample system, and polarization state detector comprising component(s) after said sample system;

it comprises at least three chamber regions, in one of which is present polarization state generator comprising component(s) prior to said sample system, in the second of which is present the sample system and in the third of which is present polarization state detector comprising component(s) after said sample system;

it comprises at least two chamber regions, in one of which is present polarization state generator comprising component(s) prior to said sample system and said sample system, and in the second of which is present polarization state detector comprising component(s) after said sample system;

it comprises at least two chamber regions, in one of which is present polarization state generator comprising component(s) prior to said sample system, and in the second of which is present polarization state detector comprising component(s) after said sample system and said sample system.

\* \* \* \* \*